(12) United States Patent
Ingenito et al.

(10) Patent No.: US 9,561,301 B2
(45) Date of Patent: Feb. 7, 2017

(54) LUNG VOLUME REDUCTION THERAPY USING CROSSLINKED NON-NATURAL POLYMERS

(71) Applicant: Pulmonx, Redwood City, CA (US)

(72) Inventors: Edward P. Ingenito, North Quincy, MA (US); James A. Krom, Belmont, MA (US); Alexander Schwarz, Brookline, MA (US); Larry W. Tsai, Boston, MA (US)

(73) Assignee: Aeris Therapeutics, LLC, Woburn, MA (US)

( * ) Notice: Subject to any disclaimer, the term of this patent is extended or adjusted under 35 U.S.C. 154(b) by 0 days.

(21) Appl. No.: 14/686,306

(22) Filed: Apr. 14, 2015

(65) Prior Publication Data

US 2015/0217020 A1 Aug. 6, 2015

Related U.S. Application Data

(62) Division of application No. 13/898,624, filed on May 21, 2013, now Pat. No. 9,006,340, which is a division of application No. 13/493,409, filed on Jun. 11, 2012, now Pat. No. 8,445,589, which is a division of application No. 12/117,367, filed on May 8, 2008, now Pat. No. 8,198,365.

(60) Provisional application No. 60/917,419, filed on May 11, 2007.

(51) Int. Cl.
*A61L 24/04* (2006.01)
*C08J 3/075* (2006.01)
*A61L 24/00* (2006.01)

(52) U.S. Cl.
CPC .......... *A61L 24/043* (2013.01); *A61L 24/0031* (2013.01); *C08J 3/075* (2013.01); *C08J 2329/04* (2013.01)

(58) Field of Classification Search
CPC ..... A61L 24/0031; A61L 24/043; C08J 3/075; C08J 2329/04
See application file for complete search history.

(56) References Cited

U.S. PATENT DOCUMENTS

| 5,383,899 | A | * | 1/1995 | Hammerslag | .... A61B 17/00491 128/898 |
| 2005/0070759 | A1 | * | 3/2005 | Armstrong | ........... A61B 1/0051 600/105 |
| 2006/0009801 | A1 | * | 1/2006 | McGurk | .......... A61B 17/00491 606/214 |
| 2006/0210602 | A1 | * | 9/2006 | Sehl | ...................... A61L 17/145 424/423 |

OTHER PUBLICATIONS

Baron, T.H., et al.; Pan Vascular Medicine, 2002, p. 1712-1724.*

* cited by examiner

*Primary Examiner* — Robert Jones, Jr.
(74) *Attorney, Agent, or Firm* — Dana M. Gordon; Foley Hoag LLP

(57) ABSTRACT

One aspect of the invention relates to a hydrogel comprising a non-natural polymer comprising a plurality of pendant nucleophilic groups and a crosslinker comprising at least two pendant electrophilic groups. Another aspect of the invention relates to a hydrogel comprising a non-natural polymer comprising a plurality of pendant electrophilic groups and a crosslinker comprising at least two pendant nucleophilic groups. Yet another aspect of the invention relates to a method for reducing lung volume in a patient comprising the step of administering a hydrogel composition as described herein. Further, hydrogels of the invention may be used to achieve pleurodesis, seal brochopleural fistulas, seal an air leak in a lung, achieve hemostasis, tissue sealing (e.g., blood vessels, internal organs), or any combination thereof. In certain embodiments, the compositions and methods described herein are intended for use in the treatment of patients with emphysema.

21 Claims, 8 Drawing Sheets

Figure 2

Table 1. Test articles

| Test article | Source | Product# | Lot# |
|---|---|---|---|
| aPVA 2 mol% amino substituted | Aeris | | 102-107 |
| GA | Acros | 11998-0010 | B0507526 |

Table 2. Treatment groups

| Sheep | aPVA (%) | GA(%) | Right | | | Left | | | Follow-up(days) |
|---|---|---|---|---|---|---|---|---|---|
| | | | sites | gel | foam | sites | gel | foam | |
| 316 | 2.5 | .25 | 4 | 5 | 15 | 4 | 5 | 15 | 8 |
| 343 | 2.025 | .25 | 4 | 5 | 15 | 4 | 5 | 0 | 7 |
| 385 | 2.025 | .20 | 3 | 5 | 15 | 3 | 5 | 0 | 6 |

Table 3. CT scan findings

| Sheep | Change in CT volume (mL) per site treated | |
|---|---|---|
| | Post | 1 wk |
| 316 | -8 | -63.4 |
| 343 | -32.5 | -32.9 |
| 385 | -44.7 | -58.5 |

Figure 8

Table 5. Polymerization Times for aPVA/Glutaraldehyde.

| aPVA MW | % amination | aPVA concentration | Glutaraldehyde concentration [%] | pH | Polymerization Time [sec] |
|---|---|---|---|---|---|
| 170 kDa | 2.1 % | 2.6 % | 3.0 % | 4.75 | 260 |
| 170 kDa | 1.0 % | 1.8 % | 2.0 % | 5.25 | 500 |
| 40 kDa | 1.9 % | 2.6 % | 3.0 % | 5.25 | 480 |
| 100 kDa | 2.2 % | 2.6 % | 2.0 % | 5.0 | 210 |
| 100 kDa | 1.6 % | 1.8 % | 2.0 % | 5.50 | 235 |
| 100 kDa | 1.0 % | 1.8 % | 2.0 % | 5.50 | 465 |
| 100 kDa | 1.4 % | 2.0 % | 2.5 % | 6.0 | 110 |
| 100 kDa | 1.5 % | 2..4 % | 3.0 % | 6.25 | 85 |
| 100 kDa | 1.2 % | 1.8 % | 3.0 % | 6.25 | 65 |

LUNG VOLUME REDUCTION THERAPY USING CROSSLINKED NON-NATURAL POLYMERS

RELATED APPLICATIONS

This application is a divisional of U.S. patent application Ser. No. 13/898,624, filed May 21, 2013, now U.S. Pat. No. 9,006,340, which is a divisional of U.S. patent application Ser. No. 13/493,409, filed Jun. 11, 2012, now U.S. Pat. No. 8,445,589, which is a divisional of U.S. patent application Ser. No. 12/117,367, filed May 8, 2008, now U.S. Pat. No. 8,198,365, which claims the benefit of priority to U.S. Provisional Patent Application Ser. No. 60/917,419, filed May 11, 2007.

BACKGROUND

Emphysema is a common form of chronic obstructive pulmonary disease (COPD) that affects between 1.5 and 2 million Americans, and 3 to 4 times that number of patients worldwide. [American Thoracic Society Consensus Committee "Standards for the diagnosis and care of patients with chronic obstructive pulmonary disease," *Am. J. Resp. Crit. Care Med.* 1995, 152, 78-83; and Pauwels, R., et al. "Global strategy for the diagnosis, management, and prevention of chronic obstructive pulmonary disease," *Am. J. Resp. Crit. Care Med.* 2001, 163, 1256-1271.] It is characterized by destruction of the small airways and lung parenchyma due to the release of enzymes from inflammatory cells in response to inhaled toxins. [Stockley, R. "Neutrophils and protease/antiprotease imbalance," *Am. J. Resp. Crit. Care Med.* 1999, 160, S49-S52.] Although this inflammatory process is usually initiated by cigarette smoking, once emphysema reaches an advanced stage, it tends to progress in an unrelenting fashion, even in the absence of continued smoking [Rutgers, S. R., et al. "Ongoing airway inflammation inpatients with COPD who do not currently smoke," *Thorax* 2000, 55, 12-18.]

The class of enzymes that are responsible for producing tissue damage in emphysema are known as proteases. These enzymes are synthesized by inflammatory cells within the body and when released, they act to degrade the collagen and elastin fibers which provide mechanical integrity and elasticity to the lung. [Jeffery, P. "Structural and inflammatory changes in COPD: a comparison with asthma," *Thorax* 1998, 53, 129-136.] The structural changes that result from the action of these enzymes are irreversible, cumulative, and are associated with loss of lung function that eventually leaves patients with limited respiratory reserve and reduced functional capacity. [Spencer, S. et al. "Health status deterioration inpatients with chronic obstructive pulmonary disease," *Am. J. Resp. Crit. Care Med.* 2001, 163, 122-128; and Moy, M. L., et al. "Health-related quality of life improves following pulmonary rehabilitation and lung volume reduction surgery," *Chest* 1999, 115, 383-389.]

In contrast to other common forms of COPD, such as asthma and chronic bronchitis for which effective medical treatments exist, conventional medical treatment is of limited value in patients with emphysema. Although emphysema, asthma, and chronic bronchitis each cause chronic airflow obstruction, limit exercise capacity, and cause shortness of breath, the site and nature of the abnormalities in asthma and chronic bronchitis are fundamentally different from those of emphysema. In asthma and chronic bronchitis, airflow limitation is caused by airway narrowing due to smooth muscle constriction and mucus hyper-secretion. Pharmacologic agents that relax airway smooth muscle and loosen accumulated secretions are effective at improving breathing function and relieving symptoms. Agents that act in this way include beta-agonist and anti-cholinergic inhalers, oral theophylline preparations, leukotriene antagonists, steroids, and mucolytic drugs.

In contrast, airflow limitation in emphysema is not primarily due to airway narrowing or obstruction, but due to loss of elastic recoil pressure as a consequence of tissue destruction. Loss of recoil pressure compromises the ability to fully exhale, and leads to hyper-inflation and gas trapping. Although bronchodilators, anti-inflammatory agents, and mucolytic agents are frequently prescribed for patients with emphysema, they are generally of limited utility since they are intended primarily for obstruction caused by airway disease; these classes of compounds do nothing to address the loss of elastic recoil that is principally responsible for airflow limitation in emphysema. [Barnes, P. "Chronic Obstructive Pulmonary Disease," *N. Engl. J. Med.* 2000, 343(4), 269-280.]

While pharmacologic treatments for advanced emphysema have been disappointing, a non-medical treatment of emphysema has recently emerged, which has demonstrated clinical efficacy. This treatment is lung volume reduction surgery (LVRS). [Flaherty, K. R. and F J. Martinez "Lung volume reduction surgery for emphysema," *Clin. Chest Med.* 2000, 21(4), 819-48.]

LVRS was originally proposed in the late 1950s by Dr. Otto Brantigan as a surgical remedy for emphysema. The concept arose from clinical observations which suggested that in emphysema the lung was "too large" for the rigid chest cavity, and that resection of lung tissue represented the best method of treatment since it would reduce lung size, allowing it to fit and function better within the chest. Initial experiences with LVRS confirmed that many patients benefited symptomatically and functionally from the procedure. Unfortunately, failure to provide objective outcome measures of improvement, coupled with a 16% operative mortality, led to the initial abandonment of LVRS.

LVRS was accepted for general clinical application in 1994 through the efforts of Dr. Joel Cooper, who applied more stringent pre-operative evaluation criteria and modern post-operative management schemes to emphysema patients. [Cooper, J. D., et al. "Bilateral pneumonectomy for chorale obstructive pulmonary disease," *J. Thorac. Cardiovasc. Surg.* 1995, 109, 106-119.] Cooper reported dramatic improvements in lung function and exercise capacity in a cohort of 20 patients with advanced emphysema who had undergone LVRS. There were no deaths at 90-day follow-up, and physiological and functional improvements were markedly better than had been achieved with medical therapy alone.

While less dramatic benefits have been reported by most other centers, LVRS has nevertheless proven to be effective for improving respiratory function and exercise capacity, relieving disabling symptoms of dyspnea, and improving quality of life in patients with advanced emphysema. [Gelb, A. F., et al. "Mechanism of short-term improvement in lung function after emphysema resection," *Am. J. Respir. Crit. Care Med.* 1996, 154, 945-51; Gelb, A. F., et al. "Serial lung function and elastic recoil 2 years after lung volume reduction surgery for emphysema," *Chest* 1998, 113(6), 1497-506; Criner, G. and G. E. D'Alonzo, Jr., "Lung volume reduction surgery: finding its role in the treatment of patients with severe COPD," *J. Am. Osteopath. Assoc.* 1998, 98(7), 371; Brenner, M., et al. "Lung volume reduction surgery for emphysema," *Chest* 1996, 110(1), 205-18; and Ingenito, E.

P., et al. "Relationship between preoperative inspiratory lung resistance and the outcome of lung-volume-reduction surgery for emphysema," *N. Engl. J. Med.* 1998, 338, 1181-1185.] The benefits of volume reduction have been confirmed in numerous cohort studies, several recently-completed small randomized clinical trials, and the National Emphysema Treatment Trial (NETT). [Goodnight-White, S., et al. "Prospective randomized controlled trial comparing bilateral volume reduction surgery to medical therapy alone inpatients with severe emphysema," *Chest* 2000, 118(Suppl 4), 1028; Geddes, D., et al. "L-effects of lung volume reduction surgery inpatients with emphysema," *N. Eng. J. Med.* 2000, 343, 239-245; Pompeo, E., et al. "Reduction pneumoplasty versus respiratory rehabilitation in severe emphysema: a randomized study," *Ann. Thorac. Surg.* 2000, 2000(70), 948-954; and Fishman, A., et al. "A randomized trial comparing lung-volume-reduction surgery with medical therapy for severe emphysema," *N. Eng. J. Med.* 2003, 348(21): 2059-73.] On average, 75-80% of patients have experienced a beneficial clinical response to LVRS (generally defined as a 12% or greater improvement in FEV, at 3 month follow-up). The peak responses generally occur at between 3 and 6 months post-operatively, and improvement has lasted several years. [Cooper, J. D. and S. S. Lefrak "Lung-reduction surgery: 5 years on," *Lancet* 1999, 353 (Suppl 1), 26-27; and Gelb, A. F., et al. "Lung function 4 years after lung volume reduction surgery for emphysema," *Chest* 1999, 116(6), 1608-15.] Results from NETT have further shown that in a subset of patients with emphysema, specifically those with upper lobe disease and reduced exercise capacity, mortality at 29 months is reduced.

Collectively, these data indicate that LVRS improves quality of life and exercise capacity in many patients, and reduces mortality in a smaller fraction of patients, with advanced emphysema. Unfortunately, NETT also demonstrated that the procedure is very expensive when considered in terms of Quality Adjusted Life Year outcomes, and confirmed that LVRS is associated with a 5-6% 90 day mortality. [Chatila, W., S. Furukawa, and G. J. Criner, "Acute respiratory failure after lung volume reduction surgery," *Am. J. Respir. Crit. Care Med.* 2000, 162, 1292-6; Cordova, F. C. and G. J. Criner, "Surgery for chronic obstructive pulmonary disease: the place for lung volume reduction and transplantation," Curr. Opin. Pulm. Med. 2001, 7(2), 93-104; Swanson, S. J., et al. "No-cut thoracoscopic lung placation: a new technique for lung volume reduction surgery," *J. Am. Coll. Surg.* 1997, 185(1), 25-32; Sema, D. L., et al. "Survival after unilateral versus bilateral lung volume reduction surgery for emphysema," J. Thorac. Cardiovasc. Surg. 1999, 118(6), 1101-9; and Fishman, A., et al. "A randomized trial comparing lung-volume-reduction surgery with medical therapy for severe emphysema," *N. Engl. J. Med.* 2003, 348(21), 2059-73.] In addition, morbidity following LVRS is common (40-50%) and includes a high incidence of prolonged post-operative air-leaks, respiratory failure, pneumonia, cardiac arrhythmias, and gastrointestinal complications. Less invasive and less expensive alternatives that could produce the same physiological effect are desirable.

A hydrogel-based system for achieving lung volume reduction has been developed and tested, and its effectiveness confirmed in both healthy sheep, and sheep with experimental emphysema. [Ingenito, E. P., et al. "Bronchoscopic Lung Volume Reduction Using Tissue Engineering Principles," *Am. J. Respir. Crit. Care Med.* 2003, 167, 771-778.] This system uses a rapidly-polymerizing, fibrin-based hydrogel that can be delivered through a dual lumen catheter into the lung using a bronchoscope. The fibrin-based system effectively blocks collateral ventilation, inhibits surfactant function to promote collapse, and initiates a remodeling process that proceeds over a 4-6 week period. Treatment results in consistent, effective lung volume reduction. These studies have confirmed the safety and effectiveness of using fibrin-based hydrogels in the lung to achieve volume reduction therapy.

While the above-mentioned studies confirmed the efficacy of a fibrin-based system for lung volume reduction, the system is complex, comprising more than 5 different components, and fibrinogen and thrombin are blood-derived. Further, the potential patient population is so large that wide-spread use could consume all of the fibrinogen produced worldwide. Moreover, because the product is derived from blood, contamination with blood-borne pathogens is always a concern. Lastly, fibrinogen-based systems are expensive. Accordingly, there is a need to develop a less-expensive system for lung volume reduction based on synthetic polymers.

SUMMARY

One aspect of the invention relates to a hydrogel comprising a non-natural polymer comprising a plurality of pendant nucleophilic groups and a crosslinker comprising at least two pendant electrophilic groups. Another aspect of the invention relates to a hydrogel comprising a non-natural polymer comprising a plurality of pendant electrophilic groups and a crosslinker comprising at least two pendant nucleophilic groups.

One aspect of the invention relates to a hydrogel comprising a non-natural polymer comprising a plurality of pendant primary amine groups and a crosslinker. In certain embodiments the invention relates to a three-dimensional matrix of a hydrogel formed by chemically linking non-natural polymer chains with pendant primary amines using a polyaldehyde. In certain embodiments, the hydrogel composition is mixed with a gas to form a foam.

One aspect of the invention relates to a hydrogel comprising a non-natural polymer comprising a plurality of pendant primary amine groups (which have been formed from pendant hydroxyl groups by reaction with an amine-containing compound) and a crosslinker. In certain embodiments the invention relates to a three-dimensional matrix of a hydrogel formed by chemically linking non-natural polymer chains with pendant primary amines using a polyaldehyde. In certain embodiments, the hydrogel composition is mixed with a gas to form a foam.

Another aspect of the invention relates to a method for reducing lung volume in a patient comprising the step of administering a hydrogel composition as described herein. In certain embodiments, the hydrogel composition comprises a first amount of a non-natural polymer containing a plurality of pendant primary amines and a second amount of a crosslinker, thereby forming a hydrogel in said region. In certain embodiments, the crosslinker is a dialdehyde. In certain embodiments, the crosslinker is glutaraldehyde. In certain embodiment, said hydrogel composition further comprises a gas. In certain embodiments, said gas is air or oxygen.

Another aspect of the invention relates to a method for reducing lung volume in a patient comprising the step of administering a hydrogel composition as described herein. In certain embodiments, the hydrogel composition comprises a first amount of a non-natural polymer containing a plurality of pendant primary amines, wherein said non-natural polymer containing a plurality of pendant primary amines is derived from a non-natural polymer containing a plurality of pendant hydroxyl groups, and a second amount of a crosslinker, thereby forming a hydrogel in said region. In certain embodiments, the polymer containing a plurality of pendant hydroxyl groups is polyvinyl alcohol. In certain embodiments, the crosslinker is a dialdehyde. In certain embodiments, the crosslinker is glutaraldehyde. In certain embodiment, said hydrogel composition further comprises a gas. In certain embodiments, said gas is air or oxygen.

It should be appreciated that compositions of the invention also may include one or more additional compounds (e.g., therapeutic compound(s), stabilizing compound(s), antibiotic(s), growth factor(s), etc.), buffers, salts, surfactants, anti-surfactants, lipids, excipients, and/or other suitable compounds. In certain embodiments, compositions of the invention may be sterilized.

In certain embodiments, compositions of the invention may be used to achieve pleurodesis, seal brochopleural fistulas, seal an air leak in a lung, achieve hemostasis, tissue sealing (e.g., blood vessels, internal organs), or any combination thereof. In certain embodiments, the compositions and methods described herein are intended for use in the treatment of patients with emphysema.

In certain embodiments, the compositions and methods cause minimal toxicity, are injectable through a catheter, and polymerize rapidly enough to prevent solution from spilling back into the airways following injection. Additional advantages and novel features of the present invention will become apparent from the following detailed description of various non-limiting embodiments of the invention.

BRIEF DESCRIPTION OF THE FIGURES

FIG. 2 tabulates (Table 1) test articles; treatment groups (Table 2); CT scan findings (Table 3).

FIG. 8 depicts tabulated (Table 5) polymerization times for aPVA/Glutaraldehyde.

DETAILED DESCRIPTION

Figure 1:
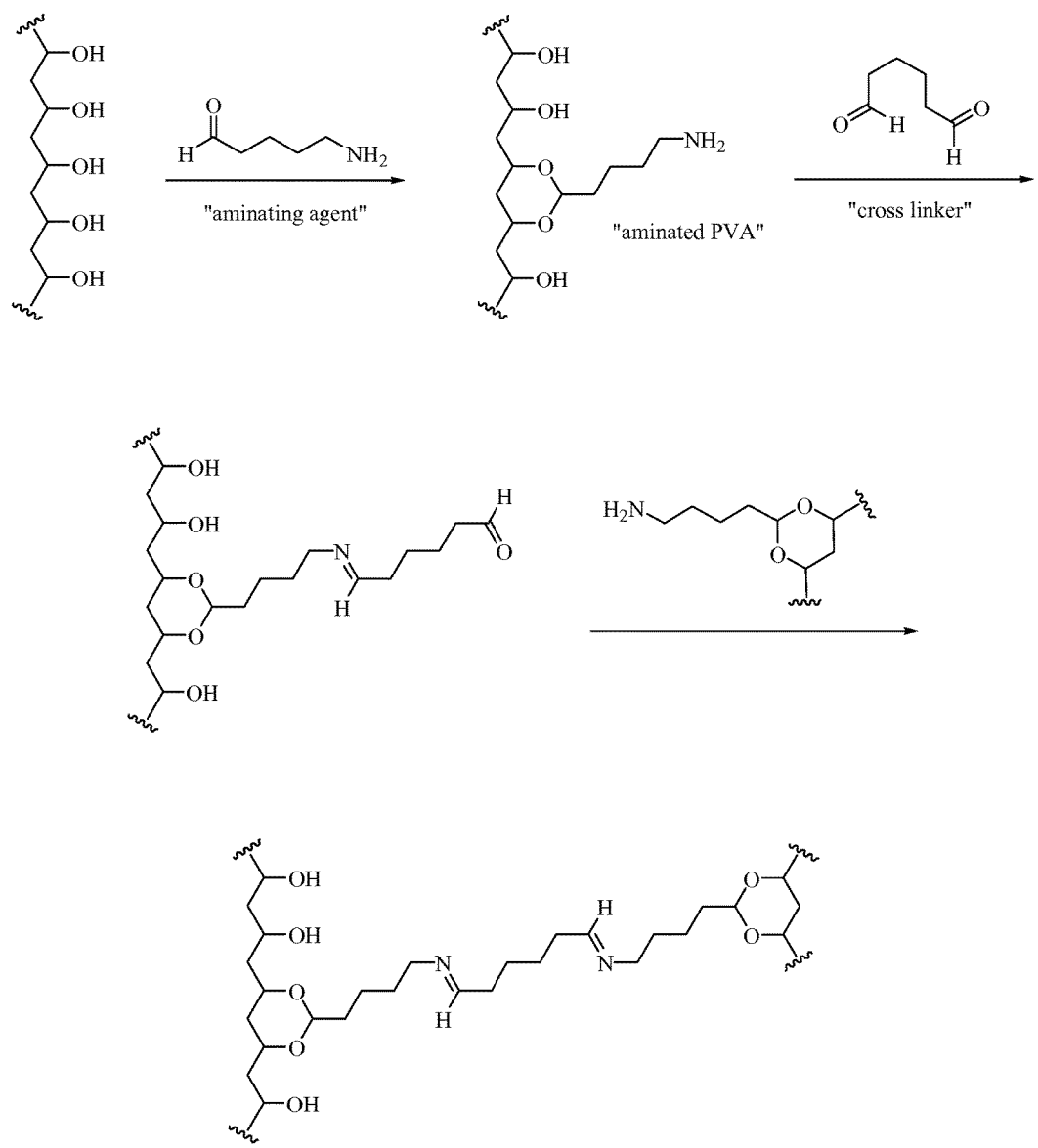
FIG. 1 depicts a reaction of polyvinyl alcohol (PVA) with an aminating agent (e.g., electrophile tethered to a primary amine) to form an aminated PVA (aPVA); reaction of the aminated PVA with a cross-linking agent (e.g., a dialdehyde); and cross-linking of the resulting product with an aPVA.

One aspect of the invention relates to compositions and methods for treatment of patients with advanced emphysema. In certain embodiments, the invention relates to a system for achieving lung volume reduction therapy, wherein an inventive composition is injected into the lung.

The composition serves several key functions that are beneficial for promoting lung volume reduction: it blocks collateral ventilation by coating the interstices of the lung surface, a step that prevents rapid re-inflation of the treatment area; it helps to ensure that reagents remain localized to the treatment area, since upon polymerization, the composition becomes trapped in the small airways and alveoli of the lung, preventing flow beyond the intended treatment site; and it fills the treatment area, displacing air and forming a bridge between adjacent regions of lung tissue.

In certain embodiments, the composition is biodegradable or resorbable; therefore, the surrounding tissues may respond by degrading the composition and cells may start growing into the composition. The biological matrix deposited by these cells links the adjacent areas of tissue and may provide a permanent tissue bridge that ensures a durable volume reduction response.

In certain embodiments, to be effective as a volume reducing agent in the lung, the precursors of the composition must have sufficiently fast polymerization kinetics and physical properties to allow for endoscopic delivery. The compositions must show rapid polymerization, and have mechanical properties such that following polymerization the firmness of the composition does not mechanically injure adjacent soft lung tissues. Further, the compositions must have initial viscosities that will allow them to be injected through a small-bore catheter. In addition, the composition must have acceptable pharmacokinetic degradation profiles in vivo. The inventive compositions described herein which posses some or all of these features should be satisfactory for achieving bronchoscopic lung volume reduction therapy.

Herein are described compositions that possess some or all of these properties. In addition, in certain embodiments, the cross-linked polymer compositions of the invention may show superior properties to some known LVRT compositions because of improved tissue adhesion; the compositions of the invention may have minimal seepage and may be self-healing (i.e., substantially less cracks or breaks might be formed in the solidified mass).

There are many advantages to the compositions and methods described herein. In some respects, the compositions described herein are chemically simpler than various current LVRT compositions. In certain embodiments, the chemicals are less expensive. In certain embodiments, the compositions of the invention have better space-filling characteristics than fibrin-based hydrogel systems, meaning that smaller amounts of material may be used to collapse a given lung volume. In addition, in certain embodiments, there appears to be decreased potential for systemic toxicity than with some other LVRT approaches.

Generally, in order for a cross-linked polymer system to be useful for LVRT, the polymer system must have a number of qualities, including:
1. Polymerization time long enough to allow delivery to the lung via a bronchoscopically placed catheter (approximately >1 min);
2. Fluid mechanical properties that allow injection through a bronchoscopically-guided small bore catheter; and
3. Polymerization time short enough to allow practical procedure length without spillage from the treatment site (approximately <10 min).

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "biodegradable" is intended to mean any component capable of disappearing by progressive degradation (metabolism).

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_1$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "amine" and "amino" are art-recognized and refer to both unsubstituted and substituted amines.

The term "amido" is art recognized as an amino-substituted carbonyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

Aliphatic is a $C_1$-$C_{12}$ chain, wherein one or more carbon atoms is optionally substituted with a heteroatom selected from the group consisting of oxygen, nitrogen or sulfur. Each carbon is optionally substituted with a functional group selected from the group consisting of hydroxyl, thiol, amino, alkyl, alkoxy, thioalkyl, amionalkyl, aryl, aryloxy, thioaryl, arylamino, heteroaryl and cycloalkyl. Aliphatic also includes optionally substituted $C_1$-$C_{12}$ alkenyl and alkynyl groups. Straight-chain or branched $C_1$-$C_{12}$-alkyl group is selected from the group consisting of methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

Cycloaliphatic is a $C_3$-$C_7$ cycloalkyl selected from the group consisting of cyclopropyl, cyclobutyl, cyclopentyl, cyclohexyl and cycloheptyl. The $C_3$-$C_7$ cycloalkyl is optionally substituted with 1, 2, 3, 4 or 5 substituents selected from the group consisting of hydroxyl, thiol, amino, alkyl, alkoxy, thioalkyl, amionalkyl, aryl, aryloxy, thioaryl, arylamino, heteroaryl and cycloalkyl.

Aromatic is an aryl group selected from the group consisting of phenyl, tolyl, xylyl, mesityl, naphthyl, fluorenyl, anthracenyl, phenanthrenyl, pyridyl, and naphthacenyl, wherein the aryl group is optionally substituted with 1, 2, 3, 4 or 5 substituents selected from the group consisting of alkyl, alkoxy, thioalkyl, amino, nitro, trifluoromethyl, aryl, halo and cyano. Aromatic dialdehydes include isophthalaldehyde, phthalaldehyde and terephthalaldehyde.

Heterocycloaliphatic is a $C_4$-$C_7$ ring optionally substituted with 1, 2 or 3 heteroatoms selected from the group consisting of oxygen, nitrogen and sulfur. Each carbon is optionally substituted with a functional group selected from the group consisting of hydroxyl, thiol, amino, alkyl, alkoxy, thioalkyl, amionalkyl, aryl, aryloxy, thioaryl, arylamino, heteroaryl and cycloalkyl. Heterocycloaliphatic group includes pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

Heterocyclic is a heterocycloaromatic selected from the group consisting of pyridyl, quinolinyl, acridinyl, pyridazinyl, pyrimidinyl and pyrazinyl, wherein the heterocycloaromatic is optionally substituted with 1, 2 or 3 substituents selected from the group consisting of alkyl, alkoxy, thioalkyl, amino, nitro, trifluoromethyl, aryl, halo and cyano.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Of particular interest herein, the free hydroxyl group on poly (vinyl alcohol) are nucleophiles.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, hydroxysuccinimidyl esters, lactones, lactams, maleimides, and the like. Non-cyclic electrophiles include aldehydes, imines, ketones, phosphates, iodoacetamides, sulfates, sulfonates (e.g., tosylates), halides such as chlorides, bromides, iodides, and the like.

As used herein, the term "polymer" means a molecule, formed by the chemical union of two or more monomer or oligomer units. The chemical units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers. The relationship between the polymer subunits may be oriented be head-to-head or head-to-tail relative to each subunit.

The non-natural polymers for use in the present invention comprise either a plurality of pendant electrophilic or nucleophilic groups. Examples of the non-natural polymers for use in the present invention include, but are not limited to polyalcohols such as ethylene vinyl alcohol (EVAL), hydroxyethyl acrylate, poly(ethylene glycol), poly(vinyl alcohol), poly(hydroxypropyl methacrylamide), polypropylene glycol); polyamines (such as polyvinylamine, polyallylamine, tetramethyleneamine, pentamethyleneamine, hexamethyleneamine, bis(2-hydroxyethyl)amine, bis(2-aminoethyl)amine, tris(2-aminoethyl)amine, branched or linear polyethyleneimine—e.g., Lubrasols™—and salts thereof, and derivatives of polyethyleneimine such as acylated polyetheyleneimine); dendrimers (such as PAMAM Starburst dendrimers); polyalkylene glycol derivatives (such as amine-substituted polyethylene and polypropylene glycols); polyacrylates (such as amine-substituted and alcohol-substituted polyacrylates); multi-amino PEG; polymers where the backbone polymeric structure is substituted with the following pendant nucleophilic or electrophilic groups such as PEG substituted with amines, hydroxylamine, hydrazines, thiols, xanthates, amides, hydrazides, sulfonamides, oximes, malonates, imides, aldehydes, succinimidyl, isocyanates, vinylsulfones, oxiranes, arylhalides, allylhalides, alkyl halides, esters, ethers or anhydrides.

Therefore, as used herein "a polymer with a plurality of pendant hydroxyl groups" is a polymer, as discussed above, wherein hydroxyl groups are directly bonded to the backbone of the polymer, or are connected to the polymer backbone via a tether, or both. An example of a polymer with a plurality of pendant hydroxyl groups is poly(vinyl alcohol).

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

Polyvinyl Alcohols

Polyvinyl alcohol (PVA) is a water soluble polymer which may be synthesized by hydrolysis of a polyvinyl ester, such as the acetate. PVA can refer to a full or partial hydrolysis of a polyvinyl ester, such as polyvinyl acetate, resulting in the replacement of some or all of the acetate groups with hydroxyl groups. For example, polyvinyl alcohol (PVA) may be produced by polymerization of vinyl acetate followed by hydrolysis of the polyvinyl acetate polymer. The degree of polymerization determines the molecular weight and viscosity in solution. The degree of hydrolysis (saponification) signifies the extent of conversion of the acetate moieties of polyvinyl acetate to hydroxyl moieties. For example, the degree of hydrolysis may be in the range of about 60 mol % to about 99.9 mol % and the MW (weight average molecular weight) may range from about 10,000 to about 250,000.

Non-Natural Polymer Subunits

As discussed throughout, one aspect of the invention relates to the formation and crosslinking of non-natural polymers comprising a plurality of a plurality of pendant nucleophilic groups (such as PVA) or electrophilic groups. One approach to converting polymers comprising a plurality of pendant hydroxyl groups into polymers containing a plurality of pendant primary amines is to react the polymers comprising a plurality of pendant hydroxyl groups with primary amine-containing compounds. In certain embodiments, said primary amine-containing compounds consist of one or more amine tethered to one or more electrophile, wherein said electrophile can react with a hydroxyl group. In certain embodiments, said primary amine-containing compounds are amino-aldehydes or amino-acetals. See, for example, U.S. Pat. No. 2,960,384 (Osugi et al.), hereby incorporated by reference. For another approach to forming amine functional derivatives of polymers with a plurality of pendant hydroxyls, see U.S. Pat. No. 6,107,401 (Dado et al.), hereby incorporated by reference, wherein cyclic amines were used in the place of primary amine-containing compounds.

One aspect of the invention relates to a non-natural polymer or a pharmaceutically acceptable salt thereof, wherein the non-natural polymer consists essentially of a plurality of subunits independently selected from the group consisting of

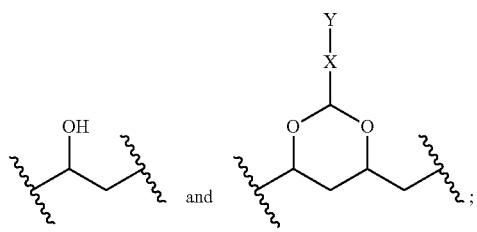

wherein independently for each occurrence
X is —(C(R)$_2$)$_n$—, —(CH$_2$OCH$_2$)$_n$CH$_2$—, —(CH$_2$)$_n$-(cycloalkyl)-(CH$_2$)$_n$—, or —(CH$_2$)$_n$-(aryl)-(CH$_2$)$_n$—;
R is H or lower alkyl;
Y is —NHR', —OH, or —SH;
R' is H, NH$_2$, aliphatic, aromatic, heterocyclic, cycloaliphatic or saturated heterocyclic moiety;
n is 1-20; and about 60 mol % to about 99 mol % of the subunits are

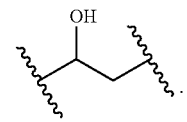 [SMILES: *CC(*)O]

In certain embodiments, the present invention relates to the aforementioned polymer, wherein X is —(C(R)$_2$)$_n$—; and R is H.

In certain embodiments, the present invention relates to the aforementioned polymer, wherein Y is NHR'; and R' is H.

In certain embodiments, the present invention relates to the aforementioned polymer, wherein X is —(C(R)$_2$)$_n$—; R is H; Y is NHR'; and R' is H.

Another aspect of the invention relates to a non-natural polymer or a pharmaceutically acceptable salt thereof, wherein the non-natural polymer consists essentially of a plurality of subunits independently selected from the group consisting of

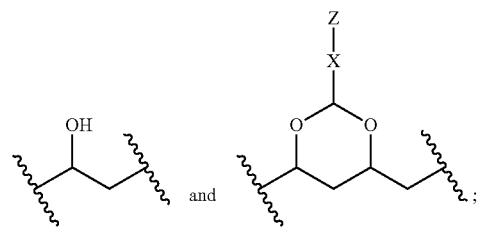

wherein independently for each occurrence
X is —(C(R)$_2$)$_n$—, —(CH$_2$OCH$_2$)$_n$CH$_2$—, —(CH$_2$)$_n$-(cycloalkyl)-(CH$_2$)$_n$—, or —(CH$_2$)$_n$-(aryl)-(CH$_2$)$_n$—;
R is H or lower alkyl;
Z is —C(O)R", —C(S)R", halide, —C(NR")R", —OP(O)(OR")$_2$, —OP(O)(OR")(R"), —OS(O)$_2$(OR"), or —OS(O)$_2$R";
R" is hydrogen, aliphatic, aromatic or heterocyclic;
n is 1-20; and about 60 mol % to about 99 mol % of the subunits are

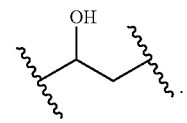

In certain embodiments, the present invention relates to the aforementioned non-natural polymer, wherein X is —(C(R)$_2$)$_n$—; and R is H.

In certain embodiments, the present invention relates to the aforementioned non-natural polymer, wherein Z is an aldehyde.

In certain embodiments, the present invention relates to the aforementioned non-natural polymer, wherein about 75 mol % to about 99 mol % of the subunits are

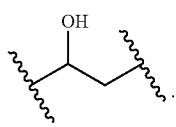 [SMILES: *CC(*)O]

In certain embodiments, the present invention relates to the aforementioned non-natural polymer, wherein about 80 mol % to about 99 mol % of the subunits are

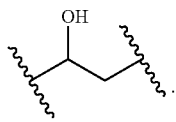 [SMILES: *CC(*)O]

In certain embodiments, the present invention relates to the aforementioned non-natural polymer, wherein about 85 mol % to about 99 mol % of the subunits are

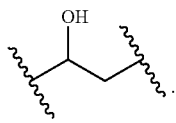 [SMILES: *CC(*)O]

In certain embodiments, the present invention relates to the aforementioned non-natural polymer, wherein about 90 mol % to about 99 mol % of the subunits are

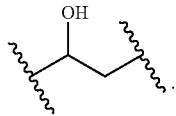 [SMILES: *CC(*)O]

In certain embodiments, the present invention relates to the aforementioned non-natural polymer, wherein about 95 mol % to about 99 mol % of the subunits are

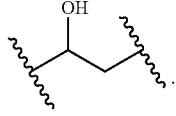 [SMILES: *CC(*)O]

In certain embodiments, the present invention relates to the aforementioned non-natural polymer, wherein n is 1-10.

In certain embodiments, the present invention relates to the aforementioned non-natural polymer, wherein n is 2-8.

In certain embodiments, the present invention relates to the aforementioned non-natural polymer, wherein n is 3-7.

In certain embodiments, the present invention relates to the aforementioned non-natural polymer, wherein n is 4-6.

Cross-Linkers

One embodiment of the present invention relates to the cross-linking of non-natural polymers. It is well known in the art that bifunctional "cross-linking" reagents contain two reactive groups, thus providing a means of covalently linking two target groups. The reactive groups of the "cross-linking" reagent may be either electrophilic or nucleophilic. When the non-natural polymer to be cross-linked comprises nucleophilic moieties, the reactive groups in a chemical cross-linking reagent typically belong to the classes of electrophilic functional groups, e.g., hydroxysuccinimidyl esters, maleimides, idoacetamides, ketones and aldehydes. However, when the non-natural polymer to be cross-linked comprises electrophilic moieties, the reactive groups in a chemical cross-linker may be nucleophilic functional groups, e.g., alcohols, thiols and amines.

Crosslinkers may also be bifunctional. Bifunctional cross-linking reagents can be divided in homobifunctional, heterobifunctional and zero-length bifunctional cross-linking reagents. In homobifunctional cross-linking reagents, the reactive groups are identical. In heterobifunctional cross-linking reagents, the reactive groups are not identical. The "zero-length" cross-linking reagent forms a chemical bond between two groups utilizing a single functional group (e.g., a carbonyl moiety derived from carbonyl diimidazole) or without itself being incorporated into the product. For example, a water-soluble carbodiimide (EDAC) may be used to couple carboxylic acids to amines. In addition to the traditional bifunctional cross-linking reagents, a noncovalent interaction between two molecules that has very slow dissociation kinetics can also function as a crosslink. For example, reactive derivatives of phospholipids can be used to link the liposomes or cell membranes to antibodies or enzymes. Biotinylation and haptenylation reagents can also be thought of as heterobifunctional cross-linking reagents because they comprise a chemically reactive group as well as a biotin or hapten moiety that binds with high affinity to avidin or an anti-hapten antibody, respectively.

In certain embodiments, the cross-linkers of the present invention are homobifunctional cross-linkers. In other embodiments, the cross-linkers of the present invention are homopolyfunctional cross-linking reagents.

In certain embodiments, the cross-linkers of the present invention are polyaldehydes. Polyaldehydes, as used herein, include compounds which contain two or more aldehyde moieties. In certain embodiments, the cross-linker of the invention is a dialdehyde. As will be appreciated by one skilled in the art, aldehydes described herein can exist as hydrates in aqueous solution, e.g., existing as hemi-acetals in aqueous solution. In certain embodiments, such hydrates can revert back to the corresponding aldehyde for cross-linking. In some embodiments, hydrates of aldehydes and/or hydrates of other cross-linking activating moieties are themselves capable of bringing about cross-linking.

In certain embodiments, the cross-linker is glutaraldehyde. It has been found that the absolute local concentration of glutaraldehyde must be maintained at or below a level that does not produce undesired excessive local toxicity. At final concentrations of 0.75% or greater, glutaraldehyde produces significant tissue necrosis in the lung. Concentrations below this level produce limited local toxicity associated with clinically acceptable side effects. In other embodiments, other polyaldehydes, such as glyoxal, may be used.

In certain embodiments, the crosslinker of the present invention is represented by the following formula:

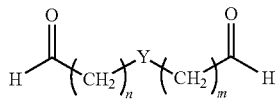

wherein independently for each occurrence
n is 0-12;
m is 0-12; and
Y is a di-radical of an aliphatic, cycloaliphatic, aromatic, heterocycloaliphatic or heterocyclic moiety.

In certain embodiments, the crosslinker of the invention is represented by the following formula:

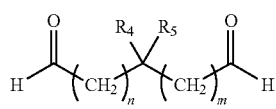

where independently for each occurrence
n is 0-12;
m is 0-12; and
$R_4$ and $R_5$ are each independently hydrogen, aliphatic, cycloaliphatic, aromatic, heterocycloaliphatic or heterocyclic moiety.

In certain embodiments, the cross-linker is water soluble at a concentration of about 0.1 mg/mL to about 5 mg/mL. In certain embodiments, the cross-linker is of biological origin. In certain embodiments, said aldehyde is an oxidized polysaccharide. In certain embodiments, the aldehyde is an oxidized polysaccharide, the polysaccharide being at least one from the group of dextran, chitin, starch, agar, cellulose, alginic acid, glycosaminoglycans, hyaluronic acid, chondroitin sulfate and derivatives thereof. In certain embodiments, the aldehdye is dextranaldehyde. The aldehyde, especially the dextranaldehyde, preferably has a molecular weight of about 60,000 to 600,000, in particular about 200,000. Higher molecular weights, in particular of at least 200,000, may result in high degrees of crosslinking.

Hydrogels

The term "hydrogels," as used herein, refers to a network of polymer chains that are water-soluble, sometimes found as a colloidal gel in which water is the dispersion medium. In other words, hydrogels are two- or multi-component systems consisting of a three-dimensional network of polymer chains and water that fills the space between the macromolecules. As used herein, hydrogels are three dimensional networks formed by cross-linked chemical subunits which upon cross-linking trap a substantial amount of water, such that the majority of their mass (typically greater than about 80%) is contributed by the entrapped water.

Hydrogels suitable for use in the invention preferably crosslink upon the addition of the crosslinker, i.e., without the need for a separate energy source. Such systems allow good control of the crosslinking process, because gelation does not occur until the mixing of the two solutions takes place. If desired, polymer solutions may contain dyes or other means for visualizing the hydrogel. The crosslinkable solutions also may contain a bioactive drug or therapeutic compound that is entrapped in the resulting hydrogel, so that the hydrogel becomes a drug delivery vehicle.

One aspect of the invention relates to a hydrogel prepared from a non-natural polymer and cross-linker; wherein said non-natural polymer comprises a plurality of pendant nucleophilic groups; and wherein said cross-linker comprises at least two pendant electrophilic groups.

In certain embodiments, the nucleophilic groups are selected from the group consisting of alcohols, amines, hydrazines, cyanides and thiols. In certain embodiments, the nucleophilic groups are selected from the group consisting of alcohols, thiols and amines. In certain embodiments, the nucleophilic groups are amines. In certain embodiments, the electrophilic groups are selected from the group consisting of aziridines, episulfides, cyclic sulfates, carbonates, imines, esters, lactones, halides, epoxides, hydroxysuccinimidyl esters, maleimides, iodoacetamides, phosphates, sulfates, sulfonates, ketones and aldehydes. In certain embodiments, the electrophilic groups are aziridines, epoxides, hydroxysuccinimidyl esters, halides, sulfonates, or aldehydes. In certain embodiments, electrophilic groups are aldehydes.

Another aspect of the invention relates to the aforementioned hydrogel, where the non-natural polymer consists essentially of a plurality of subunits independently selected from the group consisting of

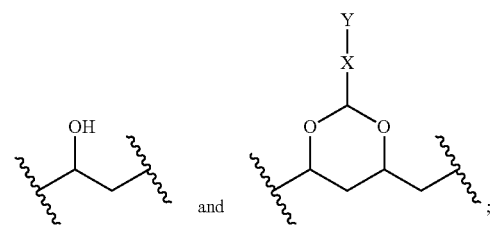

where independently for each occurrence
X is —$(C(R)_2)_n$—, —$(CH_2OCH_2)_nCH_2$—, —$(CH_2)_n$-(cycloalkyl)-$(CH_2)_n$—, or —$(CH_2)_n$-(aryl)-$(CH_2)_n$—;
R is H or lower alkyl;
Y is —NHR', —OH or —SH;
R' is hydrogen, $NH_2$, aliphatic, aromatic, heterocyclic, cycloaliphatic or a saturated heterocyclic moiety;
n is 1-20; and
about 60 mol % to about 99 mol % of the subunits are

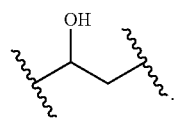

In certain embodiments, the present invention relates to the aforementioned hydrogel, wherein X is —$(C(R)_2)_n$—; and R is H.

In certain embodiments, the present invention relates to the aforementioned hydrogel, wherein Y is NHR'; and R' is H.

In certain embodiments, the present invention relates to the aforementioned hydrogel, wherein X is —$(C(R)_2)_n$—; R is H; Y is NHR'; and R' is H.

In certain embodiments, the present invention relates to the aforementioned hydrogel, wherein about 75 mol % to about 99 mol % of the subunits are

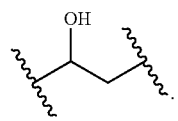

In certain embodiments, the present invention relates to the aforementioned hydrogel, wherein about 80 mol % to about 99 mol % of the subunits are

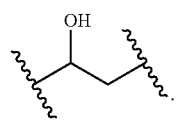

In certain embodiments, the present invention relates to the aforementioned hydrogel, wherein about 85 mol % to about 99 mol % of the subunits are

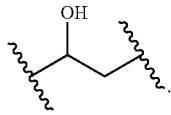

In certain embodiments, the present invention relates to the aforementioned hydrogel, wherein about 90 mol % to about 99 mol % of the subunits are

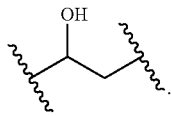

In certain embodiments, the present invention relates to the aforementioned hydrogel, wherein about 95 mol % to about 99 mol % of the subunits are

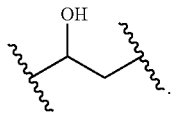

In certain embodiments, the present invention relates to the aforementioned hydrogel, wherein n is 1-10.

In certain embodiments, the present invention relates to the aforementioned hydrogel, wherein n is 2-8.

In certain embodiments, the present invention relates to the aforementioned hydrogel, wherein n is 3-7.

In certain embodiments, the present invention relates to the aforementioned hydrogel, wherein n is 4-6.

In certain embodiments, the present invention relates to the aforementioned hydrogel, wherein n is 2.

In certain embodiments, the present invention relates to the aforementioned hydrogel, wherein n is 3.

In certain embodiments, the present invention relates to the aforementioned hydrogel, wherein n is 4.

In certain embodiments, the present invention relates to the aforementioned hydrogel, wherein n is 5.

In certain embodiments, the present invention relates to the aforementioned hydrogel, wherein n is 6.

In certain embodiments, the present invention relates to the aforementioned hydrogel, wherein the weight average molecular weight of the non-natural polymer is between about 10,000 and about 500,000.

In certain embodiments, the present invention relates to the aforementioned hydrogel, wherein the weight average molecular weight of the non-natural polymer is between about 50,000 and about 250,000.

In certain embodiments, the present invention relates to the aforementioned hydrogel, wherein the crosslinker is a polyaldehyde.

In certain embodiments, the present invention relates to the aforementioned hydrogel, wherein the cross-linker is a dialdehyde.

In certain embodiments, the present invention relates to the aforementioned hydrogel, wherein the cross-linker is glutaraldehyde.

In certain embodiments, the present invention relates to the aforementioned hydrogel, wherein the crosslinker is represented by the following formula:

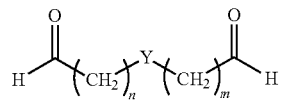

where independently for each occurrence
n is 0-12;
m is 0-12; and
Y is a di-radical of an aliphatic, cycloaliphatic, aromatic, heterocycloaliphatic or heterocyclic moiety.

In certain embodiments, the present invention relates to the aforementioned hydrogel, wherein the crosslinker is represented by the following formula:

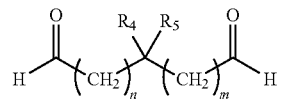

where independently for each occurrence
n is 0-12;
m is 0-12; and
$R_4$ and $R_5$ are each independently hydrogen, aliphatic, cycloaliphatic, aromatic, heterocycloaliphatic or heterocyclic moiety.

In certain embodiments, the present invention relates to the aforementioned hydrogel, wherein said cross-linker is water soluble at a concentration of about 0.1 mg/mL to about 5 mg/mL.

In certain embodiments, the present invention relates to the aforementioned hydrogel, further comprising an anti-infective.

In certain embodiments, the present invention relates to the aforementioned hydrogel, wherein said anti-infective is tetracycline.

In certain embodiments, the present invention relates to the aforementioned hydrogel, further comprising a contrast-enhancing agent.

In certain embodiments, the present invention relates to the aforementioned hydrogel, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned hydrogel, wherein upon combination of the non-natural polymer and the crosslinker substantial cross-linking occurs in about 1 minute to about 10 minutes.

In certain embodiments, the present invention relates to the aforementioned hydrogel, wherein upon combination of the non-natural polymer and the crosslinker substantial cross-linking occurs in about 1 minute to about 8 minutes.

In certain embodiments, the present invention relates to the aforementioned hydrogel, wherein upon combination of the non-natural polymer and the crosslinker substantial cross-linking occurs in about 2 minutes to about 8 minutes.

In certain embodiments, the present invention relates to the aforementioned hydrogel, wherein upon combination of the non-natural polymer and the crosslinker substantial cross-linking occurs in about 3 minutes to about 8 minutes.

In certain embodiments, the present invention relates to the aforementioned hydrogel, wherein upon combination of the non-natural polymer and the crosslinker substantial cross-linking occurs in about 4 minutes to about 8 minutes.

In certain embodiments, the present invention relates to the aforementioned hydrogel, wherein the concentration of the non-natural polymer is about 1.0% to about 10.0%.

In certain embodiments, the present invention relates to the aforementioned hydrogel, wherein the concentration of the non-natural polymer is about 1.0% to about 6.0%.

In certain embodiments, the present invention relates to the aforementioned hydrogel, wherein the concentration of the non-natural polymer is about 1.0% to about 4.0%.

In certain embodiments, the present invention relates to the aforementioned hydrogel, wherein the concentration of the non-natural polymer is about 1.5% to about 3.0%.

In certain embodiments, the present invention relates to the aforementioned hydrogel, wherein the nucleophile content of the non-natural polymer is about 0.1% to about 5.0%.

In certain embodiments, the present invention relates to the aforementioned hydrogel, wherein the nucleophile content of the non-natural polymer is about 0.25% to about 4.0%.

In certain embodiments, the present invention relates to the aforementioned hydrogel, wherein the nucleophile content of the non-natural polymer is about 1.0% to about 2.0%.

In certain embodiments, the present invention relates to the aforementioned hydrogel, wherein the pH is about 4.5 to about 9.

In certain embodiments, the present invention relates to the aforementioned hydrogel, wherein the pH is about 5 to about 7.

In certain embodiments, the present invention relates to the aforementioned hydrogel, wherein the hydrogel is in contact with a mammalian tissue.

In certain embodiments, the present invention relates to the aforementioned hydrogel, wherein the hydrogel is in contact with mammalian pulmonary tissue.

In certain embodiments, the present invention relates to the aforementioned hydrogel, wherein the hydrogel contacts an interior surface of mammalian pulmonary tissue.

In certain embodiments, the present invention relates to the aforementioned hydrogel, wherein the hydrogel contacts an interior surface of mammalian alveoli.

In certain embodiments, the present invention relates to the aforementioned hydrogel, wherein the hydrogel contacts an interior surface of mammalian alveoli and partially or completely fills the mammalian alveoli.

In certain embodiments, the present invention relates to the aforementioned hydrogel, wherein the hydrogel further comprises greater than about 90% water (w/w).

In certain embodiments, the present invention relates to the aforementioned hydrogel, wherein the hydrogel further comprises greater than about 95% water (w/w).

Another aspect of the invention relates to a hydrogel prepared from a non-natural polymer and cross-linker; wherein said non-natural polymer comprises a plurality of pendant electrophilic groups; and wherein said cross-linker comprises at least two pendant nucleophilic groups.

In certain embodiments, the electrophilic groups are selected from the group consisting of aziridines, episulfides, cyclic sulfates, carbonates, imines, esters, lactones, halides, epoxides, hydroxysuccinimidyl esters, maleimides, iodoacetamides, phosphates, sulfates, sulfonates, ketones and aldehydes. In certain embodiments, the electrophilic groups are aziridines, epoxides, hydroxysuccinimidyl esters, halides, sulfonates, or aldehydes. In certain embodiments, the electrophilic groups are aldehydes.

In certain embodiments, the nucleophilic groups are selected from the group consisting of alcohols, amines, hydrazines, cyanides, or thiols. In certain embodiments, the nucleophilic groups are selected from the group consisting of selected from the group consisting of alcohols, thiols and amines. In certain embodiments, the nucleophilic groups are amines.

In certain embodiments, the present invention relates to the aforementioned hydrogel, wherein the non-natural polymer consists essentially of a plurality of subunits independently selected from the group consisting of

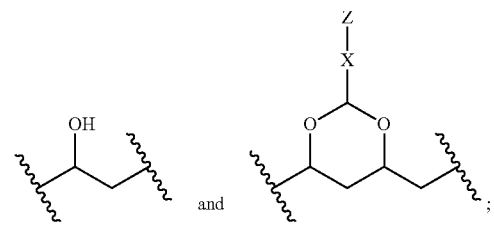

wherein independently for each occurrence
X is —(C(R)$_2$)$_n$—, —(CH$_2$OCH$_2$)$_n$CH$_2$—, —(CH$_2$)$_n$-(cycloalkyl)-(CH$_2$)$_n$—, or —(CH$_2$)$_n$-(aryl)-(CH$_2$)$_n$—;
R is H or lower alkyl;
Z is —C(O)R", —C(S)R", halide, —C(NR")R", —OP(O)(OR")$_2$, —OP(O)(OR")(R"), —OS(O)$_2$(OR"), or —OS(O)$_2$R";
R" is hydrogen, aliphatic, aromatic or heterocyclic;
n is independently for each occurrence 1-20; and
about 60 mol % to about 99 mol % of the subunits are

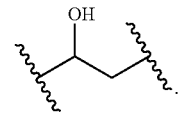

In certain embodiments, the present invention relates to the aforementioned hydrogel, wherein X is —(C(R)$_2$)$_n$— and R is H.

In certain embodiments, the present invention relates to the aforementioned hydrogel, wherein Z is an aldehyde.

In certain embodiments, the present invention relates to the aforementioned hydrogel, wherein the crosslinker is a polyamine, polyalcohol or polythiol.

In certain embodiments, the present invention relates to the aforementioned hydrogel, wherein the crosslinker is a diamine, dialcohol or dithiol.

In certain embodiments, the present invention relates to the aforementioned hydrogel, wherein the crosslinker is represented by the following formula:

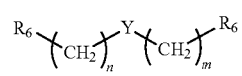

wherein independently for each occurrence
n is 0-12;
m is 0-12;

$R_6$ is selected from the group consisting of alcohols, amines, hydrazines, cyanides and thiols; and Y is a di-radical of an aliphatic, cycloaliphatic, aromatic, heterocycloaliphatic or heterocyclic moiety.

In certain embodiments, the present invention relates to the aforementioned hydrogel, wherein the crosslinker is represented by the following formula:

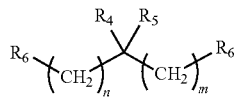

wherein independently for each occurrence
n is 0-12;
m is 0-12;
$R_4$ and $R_5$ are each independently hydrogen, aliphatic, cycloaliphatic, aromatic, heterocycloaliphatic or heterocyclic moiety; and
$R_6$ is selected from the group consisting of alcohols, amines, hydrazines, cyanides and thiols.

In certain embodiments, the present invention relates to the aforementioned hydrogel, wherein the cross-linker is water soluble at a concentration of about 0.1 mg/mL to about 5 mg/mL.

In certain embodiments, the present invention relates to the aforementioned hydrogel, further comprising an anti-infective.

In certain embodiments, the present invention relates to the aforementioned hydrogel, wherein the anti-infective is tetracycline.

In certain embodiments, the present invention relates to the aforementioned hydrogel, further comprising a contrast-enhancing agent.

In certain embodiments, the present invention relates to the aforementioned hydrogel, wherein the contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned hydrogel, wherein upon combination of the non-natural polymer and the crosslinker substantial cross-linking occurs in about 1 minute to about 10 minutes.

In certain embodiments, the present invention relates to the aforementioned hydrogel, wherein upon combination of the non-natural polymer and the crosslinker substantial cross-linking occurs in about 1 minute to about 8 minutes.

In certain embodiments, the present invention relates to the aforementioned hydrogel, wherein upon combination of the non-natural polymer and the crosslinker substantial cross-linking occurs in about 2 minutes to about 8 minutes.

In certain embodiments, the present invention relates to the aforementioned hydrogel, wherein upon combination of the non-natural polymer and the crosslinker substantial cross-linking occurs in about 3 minutes to about 8 minutes.

In certain embodiments, the present invention relates to the aforementioned hydrogel, wherein upon combination of the non-natural polymer and the crosslinker substantial cross-linking occurs in about 4 minutes to about 8 minutes.

In certain embodiments, the present invention relates to the aforementioned hydrogel, wherein the concentration of the non-natural polymer is about 1.0% to about 10.0%.

In certain embodiments, the present invention relates to the aforementioned hydrogel, wherein the concentration of the non-natural polymer is about 1.0% to about 6.0%.

In certain embodiments, the present invention relates to the aforementioned hydrogel, wherein the concentration of the non-natural polymer is about 1.0% to about 4.0%.

In certain embodiments, the present invention relates to the aforementioned hydrogel, wherein the concentration of the non-natural polymer is about 1.5% to about 3.0%.

In certain embodiments, the present invention relates to the aforementioned hydrogel, wherein the electrophile content of the non-natural polymer is about 0.1% to about 5.0%.

In certain embodiments, the present invention relates to the aforementioned hydrogel, wherein the electrophile content of the non-natural polymer is about 0.25% to about 4.0%.

In certain embodiments, the present invention relates to the aforementioned hydrogel, wherein the electrophile content of the non-natural polymer is about 1.0% to about 2.0%.

In certain embodiments, the present invention relates to the aforementioned hydrogel, wherein the pH is about 4.5 to about 9.

In certain embodiments, the present invention relates to the aforementioned hydrogel, wherein the pH is about 5 to about 7.

In certain embodiments, the present invention relates to the aforementioned hydrogel, wherein the hydrogel is in contact with a mammalian tissue.

In certain embodiments, the present invention relates to the aforementioned hydrogel, wherein the hydrogel is in contact with mammalian pulmonary tissue.

In certain embodiments, the present invention relates to the aforementioned hydrogel, wherein the hydrogel contacts an interior surface of mammalian pulmonary tissue.

In certain embodiments, the present invention relates to the aforementioned hydrogel, wherein the hydrogel contacts an interior surface of mammalian alveoli.

In certain embodiments, the present invention relates to the aforementioned hydrogel, wherein the hydrogel contacts an interior surface of mammalian alveoli and partially or completely fills the mammalian alveoli.

In certain embodiments, the present invention relates to the aforementioned hydrogel, wherein the hydrogel further comprises greater than about 90% water (w/w).

In certain embodiments, the present invention relates to the aforementioned hydrogel, wherein the hydrogel further comprises greater than about 95% water (w/w).

Ratio of Non-Natural Polymer to Cross-Linker

One aspect of the present invention relates to hydrogels prepared from the aforementioned components, wherein the ratio of the non-natural polymer to the cross-linker is greater than 5:1 (w/w). In certain embodiments, the ratio of the non-natural polymer to the cross-linker is greater than about 10:1; about 20:1; or about 50:1 (w/w). All ratios are weight ratios; in other words, a ratio of 10:1 means the weight of the non-natural polymer is ten times the weight of the cross-linker.

Foaming

In certain embodiments, the hydrogel of the invention is administered to a patient as a foam. In other embodiments, a foam of the hydrogel of the invention is formed within a lung of a patient.

In certain embodiments, a gas is used to form a foam of the hydrogel of the invention. In certain embodiments, the volume ratio of the hydrogel to the gas is about 1:1, 1:2, 1:3, 1:4, or 1:5.

In certain embodiments, the gas is non-toxic. In certain embodiments, the gas is air, helox (i.e., 79% helium and 21% oxygen), or oxygen. In certain embodiments, the gas is oxygen.

In certain embodiments, said foam is formed outside the body via shearing of a liquid composition of the invention or a component thereof with a gas through a plurality of syringes. In certain embodiments, said foam is formed outside the body via shearing of a liquid composition of the invention or a component thereof with a gas through two syringes. In certain embodiments, said foam is formed inside a lung by the action of a gas evolved from a foaming agent (e.g., a carbonate) on the liquid composition of the invention.

Foaming Modifiers

In certain embodiments, wherein a gas is added to the components from which an aforementioned composition is formed, a foaming modifier may also be added. A foaming modifier is one that facilitates the generation of a stable foam. In other words, in certain embodiments a foaming modifier may be introduced into the mixture from which a composition is formed to facilitate the formation of a foamed composition. Examples of such a foaming modifier include tissue compatible surfactants, tyloxapol, poloxamers, poloxamines, phospholipids, and glycerol. Illustrative of these foaming modifiers are non-toxic surfactants including, but are not limited to, fats or proteins in edible foams. However, the surfactant may be an ionic or non-ionic surfactant depending on the intended application.

Selected Methods of the Invention

Aspects of the invention relate to hydrogel compositions that are useful for non-surgical lung volume reduction. According to the invention, lung volume reduction, a procedure that reduces lung size by removing damaged (e.g., over-expanded) regions of the lung, can be accomplished non-surgically by procedures carried out through the patient's trachea (e.g., by inserting devices and substances through a bronchoscope), rather than by procedures that disrupt the integrity of the chest wall [Ingenito et al., *Am. J. Resp. Crit. Care Med.* 2001, 164, 295-301; Ingenito et al., *Am. J. Resp. Crit. Care Med.* 2000, 161, A750; and Ingenito et al., *Am. J. Resp. Crit. Care Med.* 2001, 163, A957.] In one aspect of the invention relates to a method for reducing lung volume in a patient, comprising the step of administering to a patient in need thereof a therapeutically effective amount of any one of the aforementioned hydrogel compositions.

In certain embodiments of the aforementioned methods, the hydrogel is administered using a bronchoscope. In other embodiments, the hydrogel is administered using a catheter.

In another aspect of the invention, non-surgical lung volume reduction is performed by introducing a material (e.g., a hydrogel) into a target region of the lung to promote collapse of the target region. In one embodiment, the material promotes stable collapse by adhering to the collapsed tissue together and/or by promoting scarring of the collapsed tissue.

Suitable bronchoscopes include those manufactured by Pentax, Olympus, and Fujinon, which allow for visualization of an illuminated field. The physician guides the bronchoscope into the trachea and through the bronchial tree so that the open tip of the bronchoscope is positioned at the entrance to target region (i.e., to the region of the lung that will be reduced in volume). The bronchoscope can be guided through progressively narrower branches of the bronchial tree to reach various subsegments of either lung. For example, the bronchoscope can be guided to a subsegment within the upper lobe of the patient's left lung.

In certain embodiments, a balloon catheter may be guided through the bronchoscope to a target region of the lung. When the catheter is positioned within the bronchoscope, the balloon is inflated so that material passed through the catheter will be contained in regions of the lung distal to the balloon.

In certain embodiments, a method of the invention results in overall lung volume reduction of about 0.5% to about 40%. In certain embodiments, a method of the invention results in overall lung volume reduction of about 0.5% to about 30%. In certain embodiments, a method of the invention results in overall lung volume reduction of about 0.5% to about 20%. In certain embodiments, a method of the invention results in overall lung volume reduction of about 0.5% to about 10%. Such reduction may be achieved upon a single or multiple administrations of compositions of the present invention.

Yet another aspect of the invention relates to a method of sealing an air leak in a lung, comprising the step of administering to a lung of a patient in need thereof a therapeutically effective amount of any one of the aforementioned hydrogel compositions, thereby sealing the air leak in the lung.

Selected Kits of the Invention

This invention also provides kits for conveniently and effectively implementing the methods of this invention. Consistent with the definitions in the preceding sections, such kits comprise a polymer having a plurality of pendant amines and a plurality of pendant hydroxyl groups, a cross-linker, and instructions for their use; and optionally a means for facilitating their use consistent with methods of this invention. Such kits provide a convenient and effective means for assuring that the methods are practiced in an effective manner. The compliance means of such kits includes any means which facilitates practicing a method of this invention. Such compliance means include instructions, packaging, and dispensing means, and combinations thereof. Kit components may be packaged for either manual or partially or wholly automated practice of the foregoing methods. In other embodiments, this invention contemplates a kit including polymers and/or cross-linkers of the present invention, and optionally instructions for their use.

Any of these kits may contain devices used in non-surgical lung volume reduction. For example, they can also contain a catheter (e.g., a single- or multi-lumen (e.g., dual-lumen) catheter that, optionally, includes a balloon or other device suitable for inhibiting airflow within the respiratory tract), tubing or other conduits for removing material (e.g., solutions, including those that carry debrided epithelial cells) from the lung, a stent or a valve or other device that may be placed in an airway to block or reduce airflow into or out of a lung or lung region, and/or a bronchoscope.

One aspect of the invention relates to a kit, comprising a first container comprising a first amount of a first mixture comprising a non-natural polymer; a second container comprising a second amount of a second mixture comprising a cross-linker; and instructions for use in lung volume reduction therapy.

In certain embodiments, the present invention relates to the aforementioned kit, further comprising a third amount of an anti-infective.

In certain embodiments, the present invention relates to the aforementioned kit, wherein said anti-infective is tetracycline.

In certain embodiments, the present invention relates to the aforementioned kit, further comprising a fourth amount of a contrast-enhancing agent.

Therapeutic Indications

In addition to being useful for treating emphysema (e.g., as described above and in the following examples), hydrogel compositions of the invention may be used in other therapeutic applications.

Another aspect of the invention may involve the use of the hydrogel compositions to seal bronchopleural fistulas. Bronchopleural fistulas may arise from, for example, airway leaks following surgery, lung trauma or invasive infection. The medical applications of the hydrogel compositions can be applied to the lung of a patient to seal airway leaks, by filling the airways and alveoli.

In certain embodiments, the present invention relates to a method of sealing a bronchopleural fistula in a patient, comprising the step of administering to a patient in need thereof a therapeutically effective amount of any one of the aforementioned hydrogel compositions, thereby sealing the fistula.

In certain embodiments, the hydrogel is administered using a bronchoscope. In other embodiments, the hydrogel is administered using a catheter.

Another aspect of the invention involves the use of the inventive compositions to achieve pleurodesis. The need for pleurodesis may arise from refractory medical therapy, such as malignant effusions and pleural space diseases. The inventive compositions can be used to fill the pleural space and thereby displace the recurrent effusions into the pleural space. In certain embodiments, the present invention relates to a method of achieving pleurodesis in a patient, comprising the step of administering to a patient in need thereof a therapeutically effective amount of any one of the aforementioned hydrogel compositions. In certain embodiments, the hydrogel is administered using a syringe. In certain embodiments, the hydrogel is administered using a catheter.

Another aspect of the invention involves the use of the inventive compositions as a sealant to seal air leaks in a lung after surgery, for example. One embodiment of the invention relates to method of sealing an air leak in a lung, comprising the step of administering to a lung of a patient in need thereof a therapeutically effective amount of any of the aforementioned hydrogel compositions, thereby sealing the air leak in the lung.

Another aspect of the invention involves a method of attaching a first tissue to a second tissue of a patient in need thereof comprising, applying to said first tissue or said second tissue or both an effective amount of the inventive compositions, thereby attaching said first tissue to said second tissue.

Another aspect of the invention involves the use of the inventive compositions as a general topical hemostat. The inventive compositions can be used to control bleeding of, for example, a torn blood vessel. One embodiment of the invention relates to a method of achieving hemostasis, comprising the step of applying to a blood vessel of a patient in need thereof a therapeutically effective amount of any of the aforementioned hydrogel compositions, thereby achieving hemostasis.

Another aspect of the invention may involve the use of the hydrogel compositions to perform emergency tamponade of bleeding vessels. Examples of bleeding vessels include, but are not limited to, major internal limb vessels, gastrointestinal bleeding or internal organ bleeding. The inventive compositions may be used to treat bleeding vessels following trauma, surgery or gastrointestinal bleeding. The hydrogel can be applied to permanently seal a bleeding vessel. The hydrogel can be applied to post surgical gastrointestinal bleeding thereby sealing the vessel and preventing ongoing blood loss.

In certain embodiments, the present invention relates to a method of administering emergency tamponade of a bleeding vessel in a patient, comprising the step of administering to a bleeding vessel of a patient a therapeutically effective amount of any one of the aforementioned hydrogel compositions, thereby sealing the vessel.

In certain embodiments, the present invention relates to a method of administering emergency tamponade to a gastrointestinal vessel in a patient, comprising the step of administering to a gastrointestinal vessel of a patient a therapeutically effective amount of any one of the aforementioned hydrogel compositions, thereby sealing the vessel.

In other embodiments, the present invention relates to a method of administering emergency tamponade to an internal organ in a patient, comprising the step of administering to an internal organ of a patient in need thereof a therapeutically effective amount of any one of the aforementioned hydrogel compositions, thereby preventing the organ from bleeding.

Another aspect of the invention may involve the use of the hydrogel compositions to seal fistulas. Examples of fistulas include, but are not limited to, fistulas arising from gastrointestinal tumors and post surgical gastrointestinal fistulas. The hydrogel compositions may be used to seal fistulas in the gastrointestinal tract arising from tumors or surgery and thereby prevent fluid leakage into the surrounding site. The inventive compositions may be applied to permanently seal a gastrointestinal fistula. In one embodiment of the invention relates to a method of sealing a fistula in a patient, comprising the step of administering to the gastrointestinal tract of a patient in need thereof a therapeutic amount of any one of the aforementioned hydrogel compositions, thereby sealing the fistula.

EXEMPLIFICATION

The invention now being generally described, it will be more readily understood by reference to the following examples, which are included merely for purposes of illustration of certain aspects and embodiments of the present invention, and are not intended to limit the invention.

Example One

SYNTHESIS OF 2% 4-AMINOBUTYRALDEHYDE-FUNCTIONALIZED POLYVINYL ALCOHOL (2% ABA-PVA). A 7.5% aqueous solution of polyvinyl alcohol (PVA; MW of about 100,000) was prepared by dissolving 37.5 g of PVA in 462.50 g of DI water at 90° C. The solution was allowed to cool to room temperature after the PVA had completely dissolved. To the PVA solution was added 0.91 mL (4.66 mmol) of 4-aminobutyraldehyde dimethyl acetal (ABA acetal), followed by 4.46 g (45.2 mmol) of 37% aqueous hydrochloric acid. The solution was stirred overnight, and the pH was adjusted to approximately 7 using 10 M sodium hydroxide. Approximately 6.10 g (45.8 mmol) of sodium hydroxide solution was required for the neutralization. The solution was slowly added to 2 L of 99% isopropanol with vigorous stirring. The solid precipitate was collected and dissolved in 450 mL of DI water. The precipitation from isopropanol was repeated two more times, and the solid product was collected and lyophilized.

SYNTHESIS OF 4% 4-AMINOBUTYRALDEHYDE-FUNCTIONALIZED POLYVINYL ALCOHOL (4% ABA-

PVA). The same procedure as for 2% ABA-PVA was followed, except 1.83 mL (9.32 mmol) of ABA acetal and 4.92 g (49.9 mmol) of 37% aqueous HCl were used.

SYNTHESIS OF 6% 4-AMINOBUTYRALDEHYDE-FUNCTIONALIZED POLYVINYL ALCOHOL (6% ABA-PVA). The same procedure as for 2% ABA-PVA was followed, except 2.73 mL (13.98 mmol) of ABA acetal and 5.84 g (59.2 mmol) of 37% aqueous HCl were used.

Example Two

AMINATED PVA/GA IN VIVO EXPERIMENTS IN SHEEP. The following procedures were used to determine the efficacy and safety of aminated polyvinyl alcohol (aPVA) and glutaraldehyde (GA) based tissue glues for bronchoscopic lung volume reduction (BLVR). aPVA/GA mixtures with desirable properties for BLVR were identified through a series of in vitro experiments (described below). These formulations were then used to perform BLVR in sheep GENERAL PROCEDURES. Anesthesia was induced with ketamine 2 mg/kg, midazolam 0.3 mg/kg, and propofol 70 mg IV and maintained with propofol continuous infusion. Animals were intubated fiberoptically with a 10 mm oral endotracheal tube and mechanically ventilated with RR 12, TV 500. A baseline CT scan was obtained at 25 cmH$_2$O transpulmonary pressure, measured with an esophageal balloon.

The bronchoscope was wedged in a target segmental airway. The delivery catheter was passed through the working channel of the bronchoscope until its tip was visible 1-2 cm beyond the end of the bronchoscope. The GA solution was added to the aPVA solution. For foam treatments, foam was generated by pushing the liquid and oxygen from a wall source repeatedly through two syringes connected by a three-way stopcock. For gel treatments, the aPVA and GA were mixed using two syringes connected by a three-way stopcock, but no gas was added. The foam or gel was drawn into one of the syringes which was attached to the proximal end of the catheter and injected by hand. The catheter was then removed and air was injected through the working channel to push the foam/gel distal. After 2-3 minutes, the bronchoscope was removed from wedge position and the site was inspected for evidence of proper polymerization of the foam/gel. The bronchoscope was then wedged at the next target segment where the procedure was repeated. Following completion of the last treatment, a repeat CT scan was obtained at 25 cmH$_2$O transpulmonary pressure. Anesthesia was discontinued and the animal was extubated and allowed to recover.

All sheep were treated with 4 days of broad-spectrum antibiotics (Baytril) beginning immediately prior to LVR. Follow-up CT scans-repeat CT scans were performed at selected timepoints prior to euthanasia/necropsy. From 6-85 days following LVR, repeat CT scans were performed at 25 cmH$_2$O transpulmonary pressure. The animals were then euthanized and necropsied. The abdominal and thoracic organs were inspected. The lungs were removed enbloc and inflated and the treatment sites were evaluated semiquantitatively. The sites were then dissected and evaluated for evidence of hemorrhage, necrosis, or other gross evidence of toxicity. Tissue samples were taken from each lung treatment site as well as untreated control sites and preserved in 10% buffered formalin for later histologic processing. Samples of heart, liver, kidney, and spleen were also collected and processed in similar fashion.

Three sheep were treated with three formulations containing a range of aPVA concentrations from 2.025 to 2.5% and GA concentrations from 0.20 to 0.25%. Sheep 343 and 385 received foam treatments in the right lung and gel treatments in the left (see FIG. 2, Table 1 and Table 2).

RESULTS. All animals survived to planned euthanasia/necropsy. CT scans immediately post-LVR revealed hazy infiltrates at treatment sites in all animals (see FIG. 2, Table 3). Many of the foam-treated sites also had denser, linear appearing areas. The foam-treated sites were generally larger and more peripherally distributed. CT scans at one week revealed progression towards denser, more linear infiltrates. Volume reduction of 8 to 44.7 mL per site treated was detected by CT integration post treatment and 32.9 to 63.4 mL at one week, representing 5.3 to 12.7% volume reduction.

There were no pleural adhesions in any animal. Treatment sites were easily identified and well localized. The foam-treated sites were generally larger than the gel-treated sites. The percentage of sites with hemorrhage/necrosis ranged from 25 to 100%. For animals 343 and 385, although a larger percentage of foam sites had evidence of hemorrhage/necrosis, the actual amount of hemorrhage/necrosis at these sites was small and unlikely to be of clinical significance.

Both the foam and gel aPVA/GA mixtures tested were effective in producing lung volume reduction bronchoscopically.

Example Three

Synthesis of Aminated PVA

Each of the experiments described below was independently completed with polyvinyl alcohol of 150 kDa, 100 kDa, and 50 kDa.

2% 4-Aminobutyraldehyde-Functionalized PVA (2% ABA-PVA)

A 7.5% aqueous solution of polyvinyl alcohol (PVA) was prepared by dissolving 37.5 g of PVA in 462.50 g of DI water at 90° C. The solution was allowed to cool to room temperature after the PVA had completely dissolved. To the PVA solution was added 0.91 mL (4.66 mmol) of 4-aminobutyraldehyde dimethyl acetal (ABA acetal), followed by 4.46 g (45.2 mmol) of 37% aqueous hydrochloric acid. The solution was stirred overnight. Next the pH was adjusted to approximately 7 using 10 M sodium hydroxide. Approximately 6.10 g (45.8 mmol) of sodium hydroxide solution was required for the neutralization. The solution was slowly added to 2 L of 99% isopropanol with vigorous stirring. The solid precipitate was collected and dissolved in 800 mL of DI water by heating to 90° C. When all of the PVA is in solution, the sample was cooled to room temperature and transferred to a 3 L carboy. The sample volume was increased to approximately 2 L using additional DI water. The sample was purified by diafiltration through a 10 k MW hollow fiber column, consisting of five volume exchanges.

4% ABA-PVA

The same procedure as for 2% ABA-PVA was followed, except 1.83 mL (9.32 mmol) of ABA acetal and 4.92 g (49.9 mmol) of 37% aqueous HCl were used.

6% ABA-PVA

The same procedure as for 2% ABA-PVA was followed, except 2.73 mL (13.9 mmol) of ABA acetal and 5.37 g (54.5 mmol) of 37% aqueous HCl were used.

8% ABA-PVA

The same procedure as for 2% ABA-PVA was followed, except 3.66 mL (18.6 mmol) of ABA acetal and 5.84 g (59.2 mmol) of 37% aqueous HCl were used.

10% ABA-PVA

The same procedure as for 2% ABA-PVA was followed, except 4.57 mL (23.3 mmol) of ABA acetal and 6.29 g (63.8 mmol) of 37% aqueous HCl were used.

Figure 3:
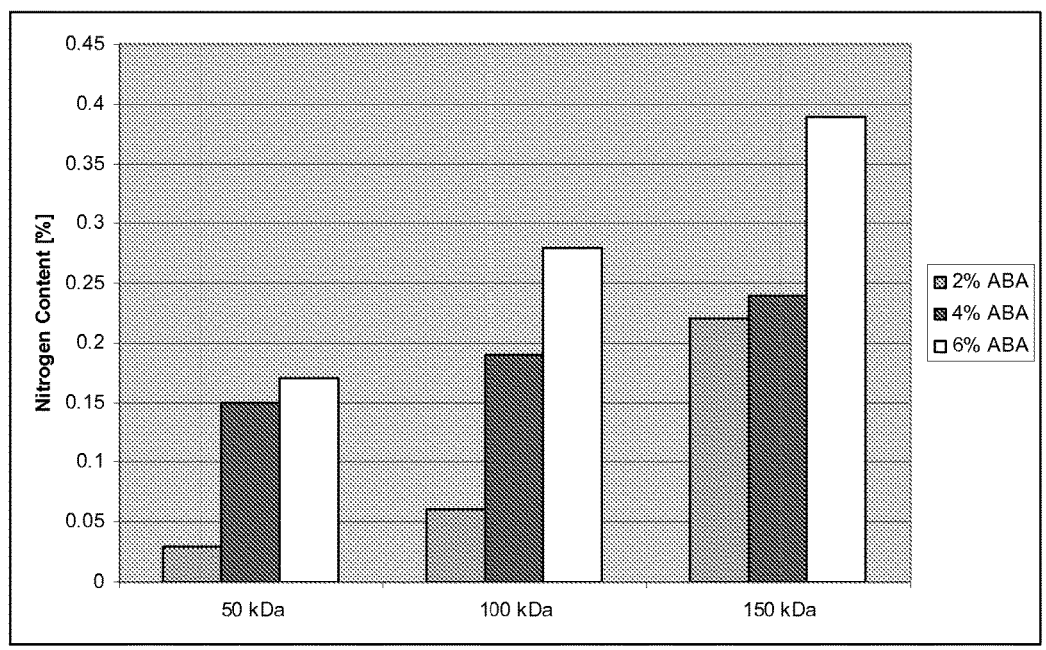
FIG. 3 depicts graphically the nitrogen content of various ABA-modified PVAs of the present invention. See Example Three.

The nitrogen contents of the products from the various syntheses were determined by elemental analysis. See FIG. 3.

Example Four

Crosslinking of Aminated PVA with Glutaric Dialdehyde

In this Example, the term "buffer" refers to a 40 mmol sodium phosphate dibasic solution that has been pH adjusted from 9.2 to 8.0 using 1 N aqueous hydrochloric acid.

Glutaric dialdehyde (GDA), 50% aqueous solution, was used to make the following three stock solutions: 1% GA=0.2 mL GA+9.8 mL Buffer; 2% GA=0.4 mL GA+9.6 mL Buffer; and 3% GA=0.6 mL GA+9.4 mL Buffer.

The ABA-PVA polymers were dissolved as 5% aqueous solutions, then diluted further to 2% solutions with buffer.

The GA and ABA-PVA solutions were combined as follows: 900 uL of polymer solution+100 uL of GA solution. This combination produced solutions with the concentrations tabulated below.

TABLE 1

Solution Concentrations

| ABA-PVA [%] | GDA [%] | Buffer [mM] |
|---|---|---|
| 1.8 | 0.3 | 25.4 |
| 1.8 | 0.2 | 25.4 |
| 1.8 | 0.1 | 25.5 |

Figure 4:
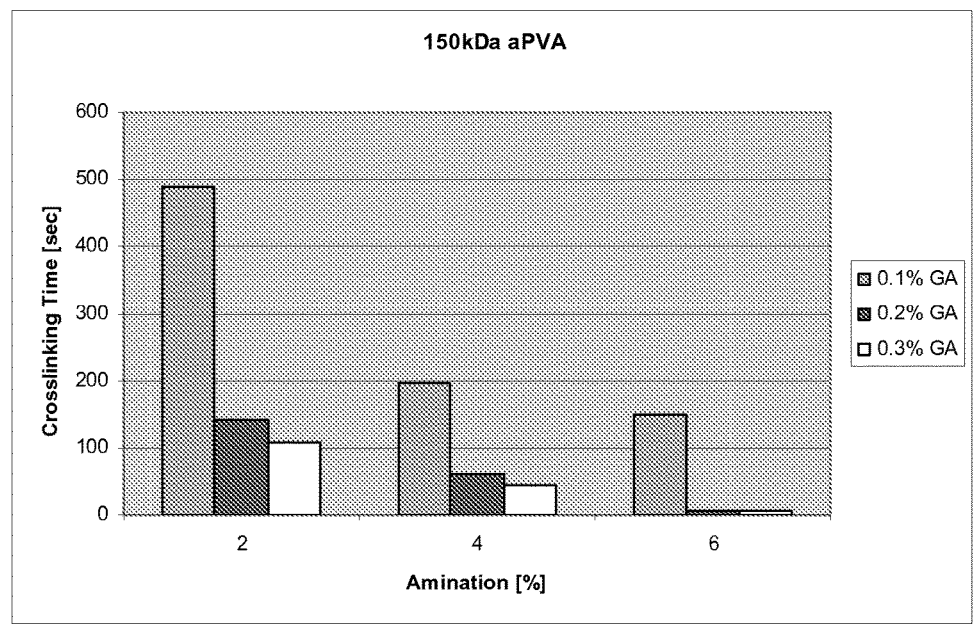
FIG. 4 depicts graphically the time to solidification for mixtures of 150 kDa ABA-PVA and GA as a function of percentage amination of the ABA-PVA and the concentration of GA. See Example Four.

The experiments were carried out according to the following procedure: 900 uL of polymer solution and 100 uL of GA solution were added to a 2 mL Eppendorf tube and vortexed for 5 seconds. The tube was inverted until the solution was not flowing and represented a solid. The time to solidification was measured. The solution concentrations yielded the results presented in FIG. 4. The data for the 150 kDa ABA-PVA samples shows a very distinct trend.

In this system both the amount of amination and the concentration of GA influence the time required to crosslink. All of the samples in this set showed a significant difference in time required to crosslink among the 0.1% GA sample and the two related samples at the same level of amination. There is also a large difference between the 2% ABA-PVA crosslinking time and the time required by the 4% and 6% ABA-PVA samples, showing that the time required to crosslink is also a function of amination.

Figure 5:
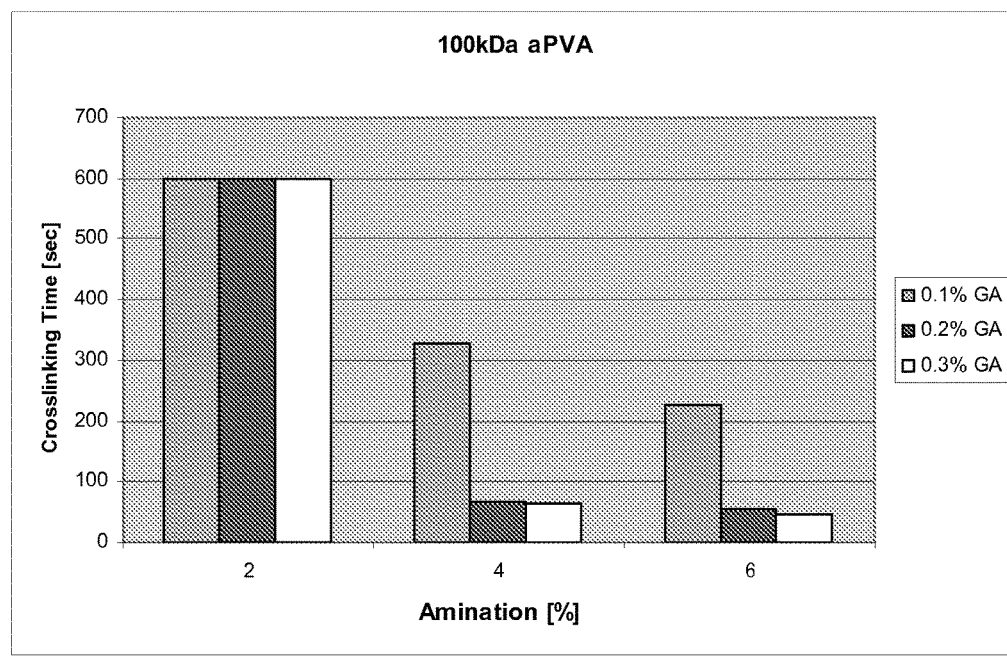
FIG. 5 depicts graphically the time to solidification for mixtures of 100 kDa ABA-PVA and GA as a function of percentage amination of the ABA-PVA and the concentration of GA. See Example Four.

The data for the 100 kDa ABA-PVA samples shows the same trend of decreasing time required to crosslink the polymer. See FIG. 5. In this set of experiments the amount of amination appears to be the major factor in the time required to crosslink. The sample with the lowest percentage of amine groups did not crosslink within 10 minutes. In the 4% and 6% ABA-PVA groups, the 0.1% GA samples took 5.5 minutes and 3.75 minutes, respectively, to solidify. The 0.2% and 0.3% GA samples took approximately one minute to crosslink.

Effect of pH on Crosslinking Times

Figure 6:
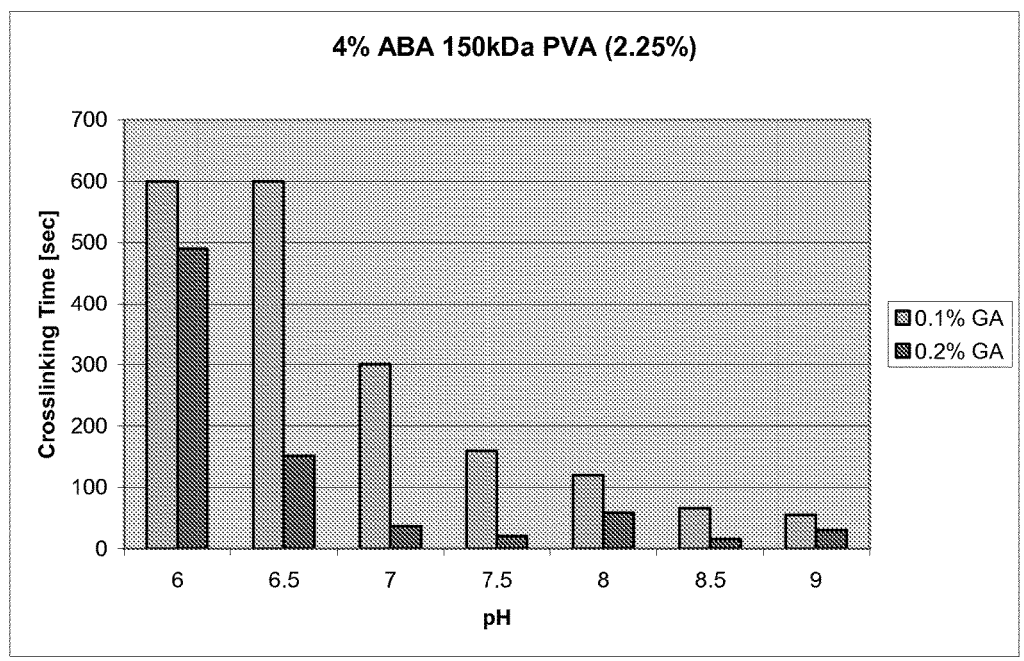
FIG. 6 depicts graphically the time to solidification for mixtures of 4% 150 kDa ABA-PVA and GA as a function of pH and the concentration of GA. See Example Four.

Phosphate buffers at 40 mmol were prepared using sodium phosphate dibasic (SPD) and then adjusted to pH values between 6 and 9. The sample tested was a 150 kDa PVA with 4% ABA in the feedstock and a nitrogen content of 0.24%. The 4% ABA-PVA polymer was dissolved as a 5% aqueous solution, then diluted further to 2.5% solution with the various buffers. 900 uL of polymer solution and 100 uL of GA solution were added to a 2 mL Eppendorf tube and vortexed for 5 seconds. The tube was inverted until the solution was not flowing and represented a solid. The time to solidification was measured. The pH had a significant effect on the time it took for the samples to crosslink. The data indicates that the time required to crosslink increases as the pH decreases. See FIG. 6.

The 4% 150 kDa ABA-PVA sample crosslinked rapidly at the higher pH range, between 7 and 9. At 0.2% GA concentration, crosslinking was still occurring at 37 seconds at pH 7. However, once the pH is adjusted to 6.5 it took nearly four times as long, 2 minutes 31 seconds, to completely crosslink. At pH 6 a sample took over 8 minutes to crosslink. The samples corresponding to 0.1% GA followed the same trend, albeit at a more gradual pace until pH 7. Below pH 7 the samples did not solidify within 10 minutes.

Example Five

In-Vivo Experiments—Part I

Four animals were treated with the Polymeric Lung Volume Reduction (PLVR) system at 5-6 sites in one lung. Clinical observations, clinical pathology, chest CT scans, and physiology were assessed immediately post-treatment and at 1, 4, 8, and 12 weeks. Chest CT scans and physiology were analyzed quantitatively to assess efficacy. Clinical observations, clinical pathology, and qualitative CT scan findings were used to assess safety. Animals were euthanized and necropsied at 12 weeks. Tissues samples were prepared for histologic evaluation.

Test materials were formulated as two components:

aPVA: a 5% solution aPVA (1.25% amine substitution) in phosphate buffer, pH~6.5 was diluted in sterile water to a concentration of 2.2%. For each treatment site, 4.5 mL was drawn into a 20 mL syringe.

Glutaraldehyde (GA): a 25% solution of glutaraldehyde was diluted in sterile water to a concentration of 2.5%. For each treatment site, 0.5 mL was drawn into a 3 mL syringe.

Following final reconstitution at the time of administration, the final concentrations were 2% aPVA and 0.25% GA. Five mL of this solution was combined with 15 mL of oxygen to generate 20 mL of foam for each treatment site. The foam crosslinked within 2-4 minutes in bench testing.

The bronchoscope was directed into wedge position at a predetermined pulmonary segment or subsegment. To verify that the bronchoscope was in proper wedge position, suction was applied and airway collapse distal to the tip of the scope was visually confirmed.

A single lumen catheter (5.5 French) was inserted through the instrument channel of the bronchoscope until the tip of the catheter was visible beyond the tip of the bronchoscope. The catheter was not advanced more than 2 cm beyond the end of the bronchoscope. If resistance was encountered, the catheter was withdrawn 0.5 to 1 cm, ensuring that the tip of the catheter was visualized beyond the tip of the bronchoscope.

The foam was prepared for injection as follows:

The 2.5% glutaraldehyde solution (0.5 mL volume) was added to the aPVA solution (4.5 mL volume) by injection through a 3-way stopcock in a 20 mL syringe. 15 mL of 100% oxygen from a wall source was added to a second 20 mL syringe. Foam was generated by pushing the liquid (5 mL starting volume) and gas (15 mL starting volume) repeatedly (approximately 20 times back and forth) through the two syringes connected by a three-way stopcock.

Injection of PLVR reagents and in situ formation of a stable foam was performed as follows:

The foam (containing aPVA, GA and oxygen) was drawn into one of the syringes and then attached to the proximal end of the catheter and injected by hand over approximately 30-40 seconds. The catheter was then removed and air was injected through the working channel of the bronchoscope to push the foam distal.

After 2-3 minutes, the bronchoscope was removed from wedge position and the site was inspected for evidence of proper polymerization of the foam. Proper polymerization was confirmed by observing no free liquid or foam flowing back from the administration site.

CT scans immediately post treatment revealed focal infiltrates at treatment sites with evidence of volume loss at some sites. CT scans at 1 week revealed dense, more linear appearing infiltrates at treatment sites with obvious volume loss and accompanying mediastinal shift toward the treatment side. CT scans at 8 and 12 weeks showed persistence of the infiltrates at treatment sites with some decrease in mediastinal shift.

CT volume integration revealed peak mean volume reduction per site treated of 154.6 mL at week 1. By week 12, volume reduction per site appeared to reach a plateau at 75.0 mL per site. Twelve-week changes from baseline in absolute R lung volume and R lung volume normalized to L lung volume were statistically significant ($p<0.008$ and $0.007$ respectively).

Figure 7:
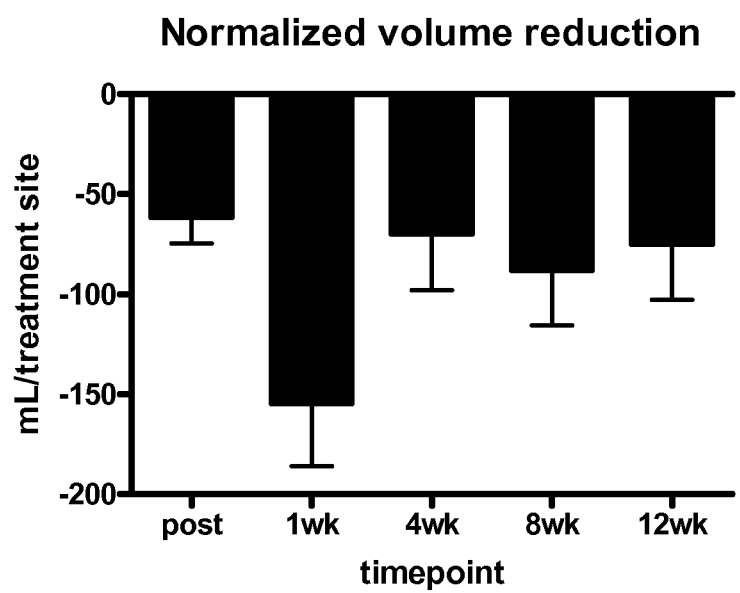
FIG. 7 depicts graphically the average normalized volume reduction per treatment site from CT integration. Error bars represent one standard deviation. See Example 5.

PLVR produced effective lung volume reduction as assessed by CT volume integration and physiology. (See FIG. 7) Clinical observations, clinical pathology, CT scans, and gross and microscopic pathology revealed no evidence of pulmonary, renal, cardiac, hepatic, or hematologic toxicity.

In-Vivo Experiments—Part II

The same in-vivo experiments were performed with the test articles buffered with citrate buffer at pH 5.0. The polymerization time of the foam was approximately 9 minutes in bench testing. This PLVR formulation produced effective lung volume reduction as assessed by CT volume integration and physiology. The average volume reduction found by CT volume integration was 158.7 ml/site at 1 week and 65.8 ml/site at 4 weeks. Clinical observations, clinical pathology, CT scans, and gross and microscopic pathology revealed no evidence of pulmonary, renal, cardiac, hepatic, or hematologic toxicity. The lung volume reductions achieved in-vivo with this system were comparable to the ones in Part 1.

In-Vivo Experiments—Part III

The same in-vivo experiments were performed with the test articles buffered with phosphate buffer at pH 6.0. The polymerization time of the foam was approximately 2 minutes in bench testing. This PLVR formulation produced effective lung volume reduction as assessed by CT volume integration and physiology. The average volume reduction found by CT volume integration was 125.6 ml/site at 1 week and 98 ml/site at 4 weeks. Clinical observations, clinical pathology, CT scans, and gross and microscopic pathology revealed no evidence of pulmonary, renal, cardiac, hepatic, or hematologic toxicity. The lung volume reductions achieved in-vivo with this system were comparable to the ones in Part I.

In-Vivo Experiments—Part IV

The same in-vivo experiments were performed with the test articles buffered with phosphate buffer at pH 6.0 and instead of oxygen, air was used to foam the liquid. The polymerization time of the foam was approximately 2 minutes in bench testing. This PLVR formulation produced effective lung volume reduction as assessed by CT volume integration and physiology. The average volume reduction found by CT volume integration was 182.3 ml/site at 1 week and 103.6 ml/site at 4 weeks. Clinical observations, clinical pathology, CT scans, and gross and microscopic pathology revealed no evidence of pulmonary, renal, cardiac, hepatic, or hematologic toxicity. The lung volume reductions achieved in-vivo with this system were comparable to the ones in Part 1.

In-Vitro Experiments

Synthesis and Purification of aPVA

A 1 L beaker and a stir bar were rinsed with WFI and to the beaker was added 497.27 g of a 7.5% PVA solution (MW 85-124 kDa, 87-89% hydrolyzed) and 7.43 g of 4-aminobutyraldehyde diethyl acetal (technical grade, minimum 90%,). The beaker was covered with aluminum foil and the solution stirred at room temperature. After one hour, 36.98 g of 10% hydrochloric acid was added to the beaker, and the solution was again covered with foil and allowed to stir at room temperature.

After about 24 hours, 1 N sodium hydroxide was added to the solution until neutral pH was reached, as indicated by pH paper and the solution was stirred at room temperature until homogenous. 1 liter of the aminated PVA ("aPVA") solution was diafiltered using a 10 kDa cut-off membrane via 9.5 exchanges with WFI. The final aPVA solution was diluted to 2.1% with phosphate buffer, pH 6.0. The amine content of the aPVA was determined by elemental analysis to be 1.43%.

By increasing or decreasing the amount of 4-aminobutyraldehyde diethyl acetal, the amine content of the aPVA polymer could be controlled between about 0.75% and 3%. Higher (146-186 kDa, average MW 170 kDa, 87-89% hydrolyzed) and lower (31-50 kDa, average MW 40 kDa, 87-89% hydrolyzed) molecular weight PVA starting materials were used to obtain aPVA utilizing the same reaction conditions.

INCORPORATION BY REFERENCE

All of the U.S. patents and U.S. published patent applications cited herein are hereby incorporated by reference.

EQUIVALENTS

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A method of achieving pleurodesis in a patient, comprising the step of administering to a patient in need thereof a therapeutically effective amount of a hydrogel, wherein said hydrogel is prepared from
   a first non-natural polymer and a first cross-linker;
   said first non-natural polymer consists essentially of a plurality of subunits independently selected from the group consisting of

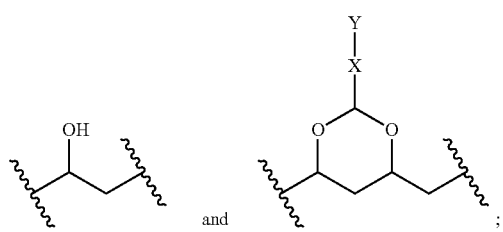

wherein independently for each occurrence
   X is —(C(R)$_2$)$_n$—, —(CH$_2$OCH$_2$)$_n$CH$_2$—, —(CH$_2$)$_n$-(cycloalkyl)-(CH$_2$)$_n$—, or —(CH$_2$)$_n$-(aryl)-(CH$_2$)$_n$—;
   R is H or lower alkyl;
   Y is —NHR', —OH, or —SH;
   R' is H, NH$_2$, aliphatic, aromatic, heterocyclic, cycloaliphatic or saturated heterocyclic moiety;
   n is 1-20; and
   about 60 mol % to about 99 mol % of the subunits are

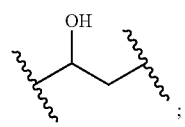

and
   said first cross-linker comprises at least two pendant first electrophilic groups,
   thereby achieving pleurodesis.

2. The method of claim 1, wherein X is —(C(R)$_2$)$_n$—; and R is H.
3. The method of claim 1, wherein Y is NHR'; and R' is H.
4. The method of claim 1, wherein X is —(C(R)$_2$)$_n$—; R is H; Y is NHR'; and R' is H.
5. The method of claim 1, wherein said first electrophilic groups are selected from the group consisting of aziridines, episulfides, cyclic sulfates, carbonates, imines, esters, lactones, halides, epoxides, hydroxysuccinimidyl esters, maleimides, iodoacetamides, phosphates, sulfates, sulfonates, ketones and aldehydes.
6. The method of claim 1, wherein said first cross-linker is a polyaldehyde.
7. The method of claim 1, wherein said first cross-linker is a dialdehyde.
8. The method of claim 1, wherein said first cross-linker is glutaraldehyde.
9. The method of claim 1, wherein said first cross-linker is represented by the following formula:

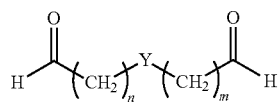

wherein independently for each occurrence
   n is 0-12;
   m is 0-12; and
   Y is a di-radical of an aliphatic, cycloaliphatic, aromatic, heterocycloaliphatic or heterocyclic moiety.

10. The method of claim 1, wherein said first cross-linker is represented by the following formula:

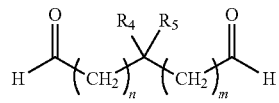

wherein independently for each occurrence
   n is 0-12;
   m is 0-12; and
   R$_4$ and R$_5$ are each independently hydrogen, aliphatic, cycloaliphatic, aromatic, heterocycloaliphatic or heterocyclic moiety.

11. A method of achieving pleurodesis in a patient, comprising the step of administering to a patient in need thereof a therapeutically effective amount of a hydrogel, wherein said hydrogel is prepared from a second non-natural polymer and a second cross-linker;
   said second non-natural polymer consists essentially of a plurality of subunits independently selected from the group consisting of

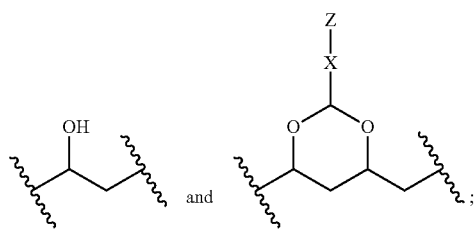

wherein independently for each occurrence

X is —(C(R)$_2$)$_n$—, —(CH$_2$OCH$_2$)$_n$CH$_2$—, —(CH$_2$)$_n$-(cycloalkyl)-(CH$_2$)$_n$—, or —(CH$_2$)$_n$(aryl)-(CH$_2$)$_n$—;

R is H or lower alkyl;

Z is —C(O)R", —C(S)R", halide, —C(NR")R", —OP(O)(OR")$_2$, —OP(O)(OR")(R"), —OS(O)$_2$(OR"), or —OS(O)$_2$R";

R" is hydrogen, aliphatic, aromatic or heterocyclic;

n is independently for each occurrence 1-20; and about 60 mol % to about 99 mol % of the subunits are

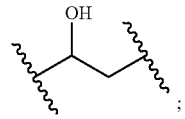

and said second cross-linker comprises at least two pendant second nucleophilic groups, thereby achieving pleurodesis.

12. The method of claim 11, wherein X is —(C(R)$_2$)$_n$— and R is H.

13. The method of claim 11, wherein Z is an aldehyde.

14. The method of claim 11, wherein X is —(C(R)$_2$)$_n$—; R is H; and Z is an aldehyde.

15. The method of claim 11, wherein said second nucleophilic groups are selected from the group consisting of alcohols, amines, hydrazines, cyanides, or thiols.

16. The method of claim 11, wherein said second cross-linker is a polyamine, polyalcohol or polythiol.

17. The method of claim 11, wherein said second cross-linker is a diamine, dialcohol or dithiol.

18. The method of claim 11, wherein said second cross-linker is represented by the following formula:

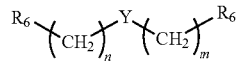

wherein independently for each occurrence n is 0-12;

m is 0-12;

R$_6$ is selected from the group consisting of alcohols, amines, hydrazines, cyanides and thiols; and Y is a di-radical of an aliphatic, cycloaliphatic, aromatic, heterocycloaliphatic or heterocyclic moiety.

19. The method of claim 11, wherein said second cross-linker is represented by the following formula:

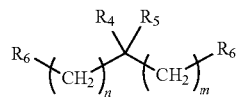

wherein independently for each occurrence n is 0-12;

m is 0-12;

R$_4$ and R$_5$ are each independently hydrogen, aliphatic, cycloaliphatic, aromatic, heterocycloaliphatic or heterocyclic moiety; and R$_6$ is selected from the group consisting of alcohols, amines, hydrazines, cyanides and thiols.

20. The method of claim 1, wherein said hydrogel is introduced into the pleural space of the patient.

21. The method of claim 11, wherein said hydrogel is introduced into the pleural space of the patient.

* * * * *